(12) United States Patent
Bassin et al.

(10) Patent No.: US 12,108,711 B2
(45) Date of Patent: Oct. 8, 2024

(54) ACTIVE POLYMER MATERIALS FOR GROWING MORE VIGOROUS, LARGER AND HEALTHIER PLANTS

(71) Applicant: HGXE Holdings, LLC, Santa Monica, CA (US)

(72) Inventors: Zev Samuel Bassin, Santa Monica, CA (US); David Drew Horinek, Santa Monica, CA (US)

(73) Assignee: Hologenix LLC, Pacific Palisades (CA)

( * ) Notice: Subject to any disclaimer, the term of this patent is extended or adjusted under 35 U.S.C. 154(b) by 768 days.

(21) Appl. No.: 15/798,088

(22) Filed: Oct. 30, 2017

(65) Prior Publication Data

US 2019/0124864 A1 May 2, 2019
US 2022/0304264 A9 Sep. 29, 2022

Related U.S. Application Data

(63) Continuation-in-part of application No. 14/860,082, filed on Sep. 21, 2015, now Pat. No. 10,694,685.
(Continued)

(51) Int. Cl.
*A01G 31/02* (2006.01)
*A01G 7/06* (2006.01)
(Continued)

(52) U.S. Cl.
CPC ............... *A01G 31/02* (2013.01); *A01G 7/06* (2013.01); *A01G 24/35* (2018.02); *A01H 4/008* (2013.01); *A01H 6/28* (2018.05); *A01G 13/0275* (2013.01)

(58) Field of Classification Search
CPC .. A01G 9/02; A01G 9/102; A01G 2009/1053; A01G 1/046; A01G 24/35; A01G 13/0275; A01G 13/0262; A01G 13/0287; A01G 24/18; A01G 9/1438; A01G 13/02; A01G 13/0231; A01G 13/0256; A01G 13/0268; A01G 22/00; A01G 22/15;
(Continued)

(56) References Cited

U.S. PATENT DOCUMENTS 3,590,528 A * 7/1971 Shepherd ............... C08L 23/20
523/125
3,839,078 A * 10/1974 Birchall .................... C08J 7/06
427/377
(Continued)

FOREIGN PATENT DOCUMENTS

CN  103224660  7/2013
EP   0579835   1/1994
(Continued)

OTHER PUBLICATIONS

Canright, Shelley, and Brian Dunbar. "Infrared Light." NASA, Mar. 18, 2004, www.nasa.gov/audience/forstudents/5-8/features/F_Infrared_Light_5-8.html. (Year: 2004).*
(Continued)

*Primary Examiner* — Christopher D Hutchens
*Assistant Examiner* — Steven J Shur
(74) *Attorney, Agent, or Firm* — Buchalter; Jared Aizad

(57) ABSTRACT

The present invention provides compositions, kits and methods for growing more vigorous, larger, and healthier plants, including from clone cuttings.

21 Claims, 3 Drawing Sheets

Related U.S. Application Data

(60) Provisional application No. 62/054,158, filed on Sep. 23, 2014.

(51) Int. Cl.
*A01G 24/35* (2018.01)
*A01H 4/00* (2006.01)
*A01H 6/28* (2018.01)
*A01G 13/02* (2006.01)

(58) Field of Classification Search
CPC .......... A01G 24/00; A01G 31/02; A01G 7/06; A01G 9/026
See application file for complete search history.

(56) References Cited

U.S. PATENT DOCUMENTS

| | | | |
|---|---|---|---|
| 3,923,729 A * | 12/1975 | Clendinning | C08K 5/00 523/125 |
| 4,442,626 A * | 4/1984 | Hammond | A01G 13/0231 47/29.1 |
| 4,741,909 A | 5/1988 | Guthrie | |
| 5,138,792 A | 8/1992 | Allingham | |
| 5,191,734 A | 3/1993 | Weber et al. | |
| 5,532,298 A | 7/1996 | Monroe et al. | |
| 5,649,495 A | 7/1997 | Salestrom | |
| 5,868,087 A | 2/1999 | Salestrom | |
| 5,879,695 A | 3/1999 | Bastiaansen et al. | |
| 5,958,294 A * | 9/1999 | Anissimov | C09K 11/06 524/129 |
| 5,998,085 A | 12/1999 | Isberg et al. | |
| 6,041,546 A | 3/2000 | Baranova | |
| 6,061,957 A | 5/2000 | Takashima | |
| 6,339,898 B1 | 1/2002 | Toye | |
| 6,560,923 B1 | 5/2003 | Kamei et al. | |
| 6,601,338 B1 | 8/2003 | Peled et al. | |
| 6,615,539 B1 | 9/2003 | Obonai et al. | |
| 7,074,499 B2 | 7/2006 | Schnurer et al. | |
| 7,247,311 B2 | 7/2007 | Stein et al. | |
| 7,342,058 B2 | 3/2008 | Peppmoller et al. | |
| 7,459,501 B2 | 12/2008 | Doane et al. | |
| 7,683,982 B2 | 3/2010 | Cho | |
| 8,017,863 B2 | 9/2011 | Forrest et al. | |
| 8,142,804 B2 | 3/2012 | Barazani | |
| 8,143,333 B2 | 3/2012 | Peppmoller et al. | |
| 8,898,955 B2 | 12/2014 | Akay et al. | |
| 9,883,637 B2 * | 2/2018 | Toye | A01G 13/0206 |
| 10,694,685 B2 | 6/2020 | Horinek | |
| 2005/0268544 A1 | 12/2005 | Maffei | |
| 2006/0185238 A1 * | 8/2006 | Burge | A01G 9/02 47/66.7 |
| 2007/0271841 A1 * | 11/2007 | Bissonnette | A01H 4/001 47/61 |
| 2008/0311392 A1 | 12/2008 | Tsu | |
| 2010/0064578 A1 | 3/2010 | Karl et al. | |
| 2010/0299993 A1 | 12/2010 | Lais et al. | |
| 2011/0308154 A1 | 12/2011 | Akay et al. | |
| 2013/0097922 A1 | 4/2013 | Lempidakis et al. | |
| 2014/0274706 A1 | 9/2014 | Hyde et al. | |
| 2014/0298511 A1 * | 10/2014 | Lewis | A61K 36/185 800/298 |
| 2014/0305036 A1 | 10/2014 | Pretsch et al. | |
| 2014/0331555 A1 | 11/2014 | Nonomura | |
| 2016/0081281 A1 * | 3/2016 | Horinek | C08K 3/36 47/1.01 R |
| 2016/0353677 A1 | 12/2016 | Toye | |
| 2017/0359967 A1 | 12/2017 | Tetrault et al. | |
| 2018/0213730 A1 | 8/2018 | Tambay et al. | |
| 2018/0310490 A1 | 11/2018 | Du et al. | |
| 2018/0371316 A1 | 12/2018 | Backfolk et al. | |
| 2019/0160796 A1 | 5/2019 | Ponti et al. | |
| 2019/0284471 A1 | 9/2019 | Gu et al. | |
| 2019/0375932 A1 | 12/2019 | Okamoto et al. | |
| 2020/0396910 A1 | 12/2020 | Horinek | |

FOREIGN PATENT DOCUMENTS

| | | |
|---|---|---|
| EP | 0964042 A | 12/1999 |
| EP | 1859674 A1 | 11/2007 |
| FR | 3000427 A1 | 7/2014 |
| KR | 10-2009-0085941 A | 8/2009 |
| WO | WO-2007/074899 A1 | 7/2007 |

OTHER PUBLICATIONS

Chang, Mei-Yun, and Wu-Jang Huang. "Production of silicon carbide liquid fertilizer by hydrothermal carbonization processes from silicon containing agricultural waste biomass." Engineering Journal, vol. 20, No. 4, Aug. 1, 2016, pp. 11-17, https://doi.org/10.4186/ej.2016.20.4.11. (Year: 2016).*
Extended European Search Report issued by the European Patent Office for Application No. 15844141.0, dated May 8, 2018, 8 pages.
Al-Helal, I. M. et al. "Measuring and Evaluating Solar Radiative Properties of Plastic Shading Nets", *Solar Energy Materials & Solar Cells*, 2011, 95, p. 677-683.
Folta et al., "Light as a Growth Regulator: Controlling Plant Biology with Narrow-bandwidth Solid-state Lighting Systems", *HortScience* 2008, vol. 43, No. 7, p. 1957-1964.
Ghosal et al, "Modeling and experimental validation of a greenhouse with evaporative cooling by moving water film over external shade cloth", *Energy and Buildings*, 2003, vol. 35, No. 8, p. 843-850.
Shibayev, P. et al. "The Effect of Circularly Polarized Light on the Growth of Plants", *International Journal of Botany*, 2011, vol. 7, No. 1, p. 113-117.
International Search Report and Written Opinion issued for PCT/US2015/051447 mailed on Dec. 14, 2015, 9 pages.
Communication Pursuant to Article 94(3) EPC for European Application No. 15844141.0, dated Jan. 5, 2022, 4 pages.
Office Action for Canadian Application No. 2962342, dated Oct. 14, 2021, 3 pages.

* cited by examiner

ACTIVE POLYMER MATERIALS FOR GROWING MORE VIGOROUS, LARGER AND HEALTHIER PLANTS

CROSS REFERENCE TO RELATED APPLICATIONS

This application is a continuation in part of U.S. patent application Ser. No. 14/860,082, filed on Sep. 21, 2015, now U.S. Pat. No. 10,694,685, which claims the benefit of U.S. Provisional Application No. 62/054,158 filed Sep. 23, 2014.

FIELD OF THE INVENTION

This invention relates to the field of agricultural cloning devices, agricultural cloning technology, seed cloning technology, seed sprouting technology, *cannabis* plant cloning technology, the *cannabis* farming industry, hydroponic systems, *cannabis* industry, and *cannabis* cloning.

BACKGROUND OF THE INVENTION

As the *cannabis* industry grows, so does the need for more efficient cloning techniques and materials. There is a need for improvements with seed and cloning materials.

There is a need for a growing medium that is reusable, recyclable and safe that accelerates the cloning process in the *cannabis* industry. "The International Agency for Research on Cancer (IARC) has reviewed the carcinogenicity of man-made mineral fibres in October 2002. The IARC Monograph's working group concluded only the more biopersistent materials remain classified by IARC as "possibly carcinogenic to humans" (Group 2B). These include refractory ceramic fibres, which are used industrially as insulation in high-temperature environments such as blast furnaces, and certain special-purpose glass wools not used as insulating materials."

As a result of the aforementioned problem, there is a need for a growing media material that has little to no carcinogenicity in that it will not leach carcinogens into the air, soil, or *cannabis* plants. There is a need for a reusable material that can be washed of all mold and bacteria while maintaining the thermal properties of the growing media. The present invention meets all of these needs and requirements.

SUMMARY OF THE INVENTION

The present invention provides methods for improving *cannabis* plant growth, said methods comprising: (a) placing an active polymer within 30 cm of the *cannabis* plant; and (b) allowing said *cannabis* plant to grow; wherein said active polymer comprises one or more minerals suspended, embedded or otherwise incorporated in a polymer matrix, and wherein an infrared radiation absorbance by said active polymer is greater than an infrared radiation absorbance by said polymer matrix alone provided the same source of a radiation; wherein said *cannabis* plant exhibits improved growth compared to a control *cannabis* plant grown without said active polymer.

The methods of the present invention encompass utilizing an active polymer that absorbs electromagnetic radiation between 400 nm to 14000 nm wavelength.

The methods of the present invention also encompass utilizing an active polymer that polarizes electromagnetic radiation between 400 nm to 14000 nm wavelength.

In other embodiments, the methods of the present invention encompass utilizing an active polymer that absorbs electromagnetic radiation and emits light between 200 and 1100 nm wavelength.

In some embodiments of the present invention, the methods utilize an active polymer that comprises one or more mineral types selected from the group consisting of silicon carbide (SiC), calcium carbide ($CaC_2$), titanium dioxide ($TiO_2$), aluminum oxide ($Al_2O_3$), and silicon dioxide ($SiO_2$).

In some embodiments, the methods of the present invention utilize an active polymer that comprises one or more polymer types selected from the group consisting of polyethylene terephthalate (PET), polyester, nylon, rayon, and spandex. In some embodiments, the present invention utilizes such polymers wherein the mineral is suspended, embedded or otherwise incorporated in the polymer matrix comprises about 1% to about 2% of a total weight of the active polymer. In some embodiments, the active polymer is extruded into a form selected from the group consisting of a fiber, a staple fiber, a film, and a sheet.

The present invention includes methods wherein the active polymer is placed in contact with the growth media for said *cannabis* plant. In some embodiments of the present invention the selected form of the active polymer is a fiber, and wherein said fiber is made into a textile using a technique selected from the group consisting of weaving, stitching, sewing, knitting, bonding, fusing, and felting.

The present invention provides kits comprising a *cannabis* plant and an active polymer, wherein said active polymer comprises one or more minerals suspended, embedded or otherwise incorporated in a polymer matrix, and wherein an infrared radiation absorbance by said active polymer is greater than an infrared radiation absorbance by said polymer matrix alone provided the same source of a radiation. In some embodiments, the kit is in a form of a bagged or a potted *cannabis* plant.

The present invention also provides kits comprising a *cannabis* plant growth media and an active polymer, wherein said active polymer comprises one or more minerals suspended, embedded or otherwise incorporated in a polymer matrix, and wherein an infrared radiation absorbance by said active polymer is greater than an infrared radiation absorbance by said polymer matrix alone provided the same source of a radiation.

In some embodiments, the kits of the present invention are in a form of a bagged or potted growth media.

The present invention also provides agricultural materials comprising an active polymer wherein said active polymer comprises one or more minerals suspended, embedded or otherwise incorporated in a polymer matrix, and wherein an infrared radiation absorbance by said active polymer is greater than an infrared radiation absorbance by said polymer matrix alone provided the same source of a radiation. In some embodiments, the agricultural materials used in the present invention comprise an active polymer covers a growth media. In some embodiments of the present invention, the agricultural material that comprises the active polymer is a bag. In some embodiments, the agricultural material that comprises the active polymer is a non-woven textile.

In some embodiments, the methods and kits of the present invention can be used for any *cannabis* plant or plant part, including *cannabis* clones, *cannabis* seedlings, parts of a *cannabis* plant, the top of a *cannabis* plant, the bottom of a *cannabis* plant, or a whole *cannabis* plant.

In some embodiments, the *cannabis* plants or plant parts used in the present invention can be or be from male or female plants.

In some embodiments, the *cannabis* plants or plant parts used in the present invention can be or be from *Cannabis indica*, *Cannabis sativa*, or a hybrid between these two species.

In some embodiments, the present invention provides methods and kits used for seed cloning technologies.

The present invention provides methods of growing a *cannabis* plant or plant part thereof comprising placing the *cannabis* plant or plant part thereof in a growing medium comprising an active polymer material, wherein the active polymer material emits light in a wavelength between about 200 nm to about 1,100 nm and absorbs ultraviolet light in the range of about 10 nm to about 400 nm; and growing the *cannabis* plant or plant thereof. In some embodiments of the present invention, these methods utilize an active polymer material that emits light in a wavelength between about 350 nm to about 800 nm.

BRIEF DESCRIPTION OF THE DRAWINGS

FIG. 1 shows the dramatic difference in *cannabis* plant top and root growth of the present invention based on using control growing media (two outside plants 104, 124) versus the present invention (middle plant 114). This example demonstrates the positive growing effects the present invention has on both the upward *cannabis* plant growth (aka above-ground growth, top growth, shoot growth) and the downward *cannabis* plant growth (aka below-ground growth, bottom growth, root growth 113).

DETAILED DESCRIPTION OF THE INVENTION

Figure 1:
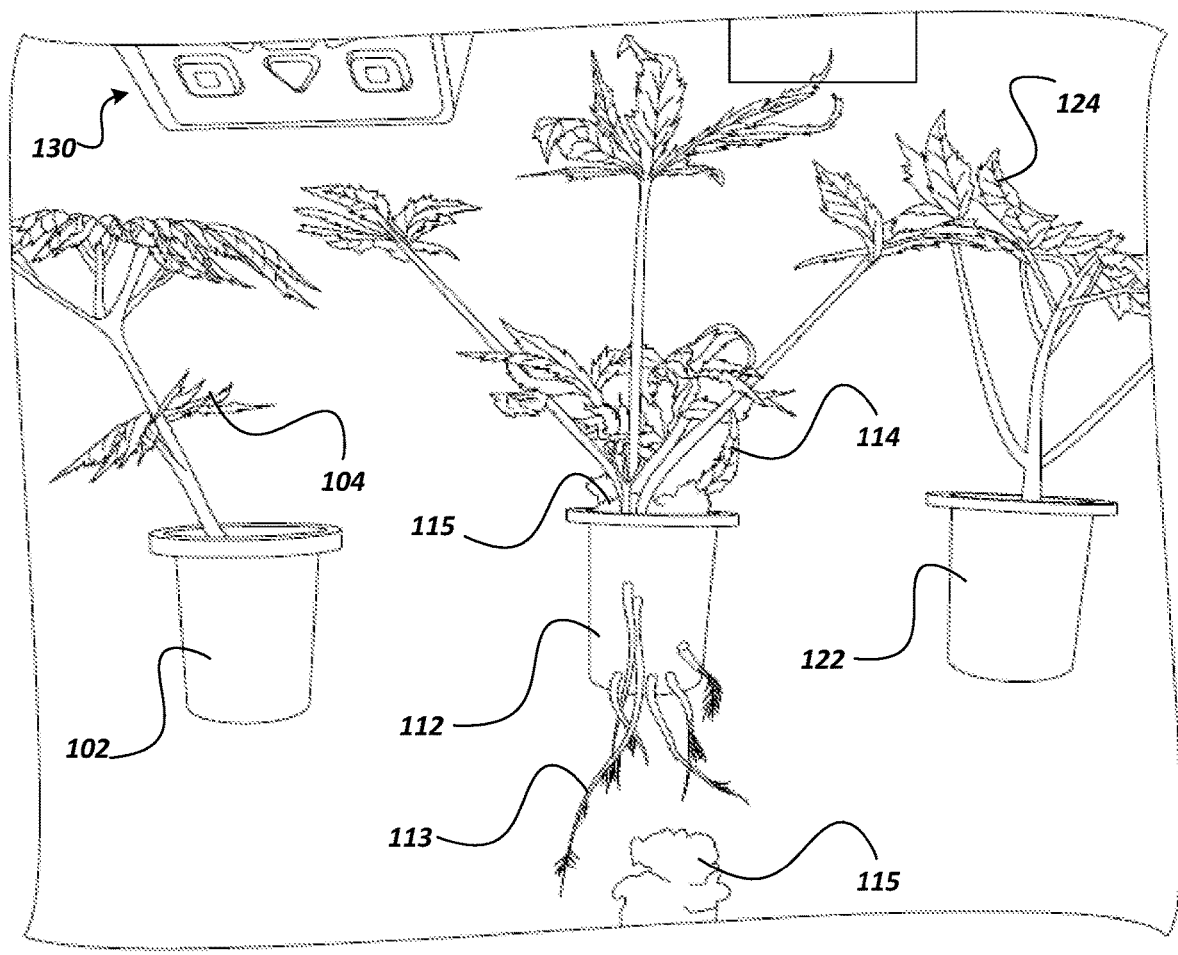
FIG. 1 is a lateral view of the control and experimental (i.e., inventive) kits for growing the *cannabis* plants.

The present invention is an improvement to growing media that are used in the *cannabis* growing industry. In one embodiment, the present invention is an improvement to the use of stone wool materials in growing plants hydroponically (e.g., RockWool™) in indoor and outdoor hydroponic growing systems. In another embodiment, the present invention is an improvement to growing bricks that are placed in growing trays for indoor and outdoor *cannabis* cloning devices.

The present invention is flexible material which allows for downward growth of a root and an upward growth of the *cannabis* plant from the sprouted clone to grow easier where the *cannabis* plant can manipulate the tensile arrangement of the present invention.

One goal of the present invention is to increase the speed and cycle time of growing *cannabis* without modifying the *cannabis* plants by using genetic engineering (i.e., biotechnological methods). Avoiding genetic engineering for *cannabis* improvement is highly desirable as genetic modification is gaining medical controversy and is being avoided by a more health-focused consumer.

The present invention comprises a polymeric fiber embedded with far infrared emissive compositions that has the ability to increase the rate of *cannabis* plant growth through thermally conductive particles embedded in the fiber of the technology.

In some embodiments, the thermal compositions of the present invention comprise one or more of the following materials that are about 1 micron (aka about 1μ or about 1 micrometer) in particle size: silicon carbide powder, zinc oxide powder and titanium dioxide powder.

In one embodiment, the polymeric composition comprises polyethylene terephthalate (otherwise known as P.E.T.).

The present disclosure addresses the need for versatile materials that can, in some embodiments, be used to improve or otherwise alter *cannabis* plant growth, development, health and/or production. In some embodiments, an active polymer material capable of harvesting photon energy is used in an agricultural setting. In some embodiments, the present invention provides a composition of an active polymer material comprising one or more minerals suspended, embedded or otherwise incorporated in a polymer matrix which is useful in an agricultural setting.

In some embodiments, the active polymer material is placed in close proximity to and/or touching a *cannabis* plant, a *cannabis* plant part, or a *cannabis* plant tissue culture. In one embodiment, the active polymer material is placed within about 30 cm from a *cannabis* plant, a *cannabis* plant part, or a *cannabis* plant tissue culture. In another embodiment, the active polymer material is placed on or mixed with the growth media in proximity to a *cannabis* plant or a *cannabis* plant part.

The active polymer material described herein exhibits interesting, useful and beneficial optical properties. In some embodiments, the active polymer material interacts with electromagnetic radiation by absorption, reflection, refraction, polarization, or wavelength shifting. In one embodiment, the active polymer material of this present disclosure absorbs a greater amount of infrared radiation when compared to a material made with only the polymer matrix provided with the same source of radiation.

In some embodiments, the active polymer material absorbs electromagnetic radiation in the range between about 400 nm (aka 400 nanometers, which equals 0.4μ) to about 14,000 nm (aka 14,000 nanometers, which equals 14μ). In some embodiments, the active polymer material polarizes electromagnetic radiation in the range between about 400 nm to about 14,000 nm. In other embodiments, the active polymer material emits light in the range between about 200 nm and about 1,100 nm. In yet another embodiment, said active polymer material emits light in the wavelength between about 350 nm and about 800 nm.

The active polymer material can be constructed into different forms and shapes, which makes this material system very versatile. In some embodiments, the active polymer material is extruded into a fiber. In some embodiments, said fiber is meshed.

In other embodiments, the active polymer material is extruded as a staple fiber. In some embodiments, the active polymer material is extruded into a film. These are additional basic forms of the active polymer material that can be further manipulated into more complex material forms. In some embodiments, any of these basic forms of the active polymer material is placed in close proximity to and/or touching a *cannabis* plant, a *cannabis* plant part, or a *cannabis* plant tissue culture.

In some embodiments, said fiber comprising the active polymer material is woven, stitched, knitted, or sewn into a textile or a fabric. In some embodiments, the textile is in a form of a bag. In a specific embodiment, the bag may be meshed. The bag may be used to hold a *cannabis* plant and its growth media. In some embodiments, said bag is filled with growth media and a *cannabis* plant is *cannabis* planted in the growth media.

In some embodiments, the textile is in the form of a sheet. In some embodiments, the sheet is meshed. In other embodiments, the sheet can be placed over the growth media. In a specific embodiment, an opening is cut out in the sheet to accommodate a stem or a trunk of the *cannabis* plant in order to place the sheet over the growth media and around the stems or trunks of the *cannabis* plants.

The fiber comprising the active polymer material is, in some embodiments, non-woven by felting, bonding, or fusing. In other embodiments, the active polymer material is non-woven into a batting material. In some embodiments, the batting material is die-cut into desired shapes such as squares, rectangles, circles, ovals, donut-like shape, or triangles, for example. In other embodiments, said die-cut material comprising the active polymer material is placed on top of the growth media and around a trunk or a stem of the *cannabis* plant.

In other embodiments, the fiber comprising the active polymer material is non-woven into a sphere-like shape, like a cotton ball, having a diameter of about 0.5 cm (aka centimeters) to about 5 cm.

In some embodiments, the sphere-like shaped material comprising the active polymer material is placed on top of the growth media and around a trunk or a stem of the *cannabis* plant. In a specific embodiment, the sphere-like shaped material is mixed in with the soil and the soil is placed around a *cannabis* plant, a *cannabis* plant part, or a *cannabis* plant tissue culture. For one example of a sphere-like shaped material, see Example 7.

The active polymer material may comprise a variety of mineral compounds.

In some embodiments, the active polymer material comprises one or more mineral types selected from the group consisting of silicon carbide (SiC), titanium dioxide ($TiO_2$), aluminum oxide ($Al_2O_3$), and silicon dioxide ($SiO_2$). In some embodiments, the total amount of all mineral comprises about 1% to about 2% of a total weight of the active polymer material.

The active polymer material may comprise one or more types of polymer matrix. In some embodiments, the active polymer material comprises one or more polymer types selected from the group consisting of polyethylene terephthalate (PET), polyester, nylon, rayon, and spandex.

The active polymer material used in agriculture, in some embodiments, is Celliant™. See U.S. Pat. No. 7,074,499, which is incorporated by reference in its entirety herein, for a description of Celliant™.

A kit can be put together with the active polymer material with those components deemed important to be used in combination. In some embodiments, a kit comprises a *cannabis* plant, a *cannabis* plant part, or a *cannabis* plant tissue culture and an active polymer material according to the present invention which is capable of harvesting photon energy. The active polymer material comprises a polymer matrix and at least one type of mineral powder, wherein the mineral powder is suspended, embedded or otherwise incorporated in the polymer matrix. In some embodiments, the active polymer material which is a part of the kit interacts with electromagnetic radiation by absorption, reflection, refraction, polarization, or wavelength shifting. In one embodiment, the active polymer material absorbs greater amount of infrared radiation when compared to a material made with only the polymer matrix and provided the same source of radiation.

In some embodiments, the kit is in the form of a bagged or a potted *cannabis* plant. In other embodiments, the kit comprises a *cannabis* plant seed, *cannabis* clone, *cannabis* stem, root, shoot, shoot plus root, or any plant part embedded or enclosed in the active polymer material.

A different kit, in some embodiments, comprises a *cannabis* planting pot or a *cannabis* planting container and an active polymer material which is capable of harvesting photon energy. The active polymer material comprises a polymer matrix and at least one type of mineral powder, wherein the mineral powder is suspended, embedded or otherwise incorporated in the polymer matrix. In some embodiments, the kit comprises a *cannabis* planting pot or a *cannabis* planting container with the active polymer material placed inside it. In other embodiments, the kit comprises the *cannabis* planting pot or the *cannabis* planting container with the active polymer material lining the inside and/or outside walls of the *cannabis* planting pot or the *cannabis* planting container.

In some embodiments, a kit comprises a *cannabis* plant growth media and an active polymer material which is capable of harvesting photon energy. Said active polymer material comprises a polymer matrix and at least one type of mineral powder, wherein the mineral powder is suspended, embedded or otherwise incorporated in the polymer matrix.

In some embodiments, the kit is in the form of a bagged growth media.

In some embodiments, one or more kits described previously comprise an active polymer material that emits light in the wavelength between about 200 nm and about 1,100 nm. In other embodiments, one or more kits described previously comprise an active polymer material that emits light in the wavelength between about 350 nm and about 800 nm. In some embodiments, one or more kits described previously comprise an active polymer material that is Celliant™.

One or more kits described herein, in some embodiments, comprise an active polymer material wherein one or more mineral types is selected from the group consisting of silicon carbide (SiC), titanium dioxide ($TiO_2$), aluminum oxide ($Al_2O_3$), and silicon dioxide ($SiO_2$). In other embodiments, one or more kits described previously comprise an active polymer material where one or more polymer type is selected from the group consisting of polyethylene terephthalate (PET), polyester, nylon, rayon, and spandex. In a specific embodiment, one or more kits mentioned previously comprise an active polymer material wherein the minerals comprise about 1% to about 2% of a total weight of the total active polymer material.

Harvesting photon energy, as mentioned earlier, encompasses a wide range of electromagnetic radiation. Some of the range in the electromagnetic spectrum is not beneficial to *cannabis* plants. In general ultraviolet light range (about 10-390 nm) may be harmful to *cannabis* plants. A material that could convert ultraviolet light range into visible light region (about 390-770 nm) would be beneficial for *cannabis* plant growth.

In some embodiments, an active polymer material capable of absorbing ultraviolet light in the range of about 10 nm to about 400 nm is used in an agricultural setting. The active polymer material comprises a polymer matrix and at least one type of mineral powder, which is suspended, embedded or otherwise incorporated in the polymer matrix. In a specific embodiment, the active polymer material is placed in close proximity to and/or touching the cannabis plant, cannabis plant part, or cannabis plant tissue culture.

In some embodiments, the active polymer material emits light in the wavelength between 200 nm and 1100 nm. In other embodiments, the active polymer material emits light in the wavelength between 350 and 800 nm in wavelength.

The active polymer material capable of absorbing ultraviolet light may be comprised of a variety of mineral compounds. In some embodiments, the active polymer material comprises one or more mineral types selected from the group consisting of silicon carbide (SiC), titanium dioxide ($TiO_2$), aluminum oxide ($Al_2O_3$), and silicon dioxide ($SiO_2$). In some embodiments, the total amount of all minerals comprises about 1% to about 2% of a total weight of said active polymer material.

The active polymer material capable of absorbing ultraviolet light may comprise one or more types of polymer matrix. In some embodiments, the active polymer material comprises one or more polymer types selected from the group consisting of polyethylene terephthalate (PET), polyester, nylon, rayon, and spandex.

The active polymer material, capable of absorbing ultraviolet light, used in agriculture, in some embodiments, is Celliant™.

Definitions

While the following terms are believed to be well understood by one of ordinary skill in the art, the following definitions are set forth to facilitate explanation of the presently disclosed subject matter.

The term "a" or "an" refers to one or more of that entity; for example, "a cannabis plant" refers to one or more cannabis plants or at least one cannabis plant. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, the verb "comprise" as is used in this description and in the claims and its conjugations are used in its non-limiting sense to mean that items following the word are included, but items not specifically mentioned are not excluded.

As used herein, the term "plant" refers to any living organism belonging to the kingdom Plantae (i.e., any genus/species in the Plant Kingdom). According to the context of its use, in some instances the term "cannabis plant" as used herein may also be intended to include any cannabis plant propagules, cannabis seedlings, cannabis clones, cannabis plant parts, or cannabis plant tissue cultures in addition to the whole cannabis plant. Such plants may or may not comprise an inflorescence.

As used herein, the term "cannabis plant part" refers to both complete cannabis plants and parts of cannabis plant. Non-limiting examples of cannabis plant part may include embryos, pollen, ovules, seeds, leaves, flowers, branches, stalks, roots, root tips, anthers, stem shoots, scions, rootstocks, cannabis plant protoplasts, cannabis plant cells including cannabis plant cells that are intact in cannabis plants and/or parts of cannabis plants, cannabis plant calli, cannabis plant clumps, cannabis plant tissues, cannabis plant tissue cultures, and the like.

As used herein, the term "cannabis plant tissue culture" refers to a composition comprising isolated cells of the same or a different type or a collection of such cells organized into parts of a cannabis plant. Non-limiting examples of cannabis plant tissue cultures include cannabis plant protoplasts, cannabis plant calli, cannabis plant clumps, and cannabis plant cells that can generate tissue culture that are intact in cannabis plants or parts of cannabis plants, such as embryos, pollen, flowers, seeds, pods, leaves, stems, roots, root tips, anthers, pistils and the like.

As used herein, the term "agricultural use" refers to use of the designated compound or a material in association with growing a cannabis plant or in association with the land used to glow cannabis plants or to raise animals for food or economic gain. Agriculture use encompasses all types of agricultural landscapes and types. Non-limiting examples of different agricultural types or technique include greenhouses, plains, fields, paddy fields, deserts, marsh, terraces, hills, fells, hydroponics, semi-hydroponics, aeroponics, fogponics, organoponics, undergrounds, tunnels, walls, indoor fields, indoor gardens, gardens, rooftops, bonsai, cannabis planters and pots, grow boxes, grow rooms, and the like.

As used herein, "improved cannabis plant growth" or "improved growth characteristic" refer to the improvement of at least one morphological, physiological and/or phenotypical characteristic of a treated cannabis plant (i.e., a test cannabis plant) when compared to an untreated cannabis plant (i.e., a control cannabis plant). Representative cannabis plant growth parameters include but are not limited to the following: above ground height, above ground cannabis plant width, root mass, number of branches, branch angle, total above ground cannabis plant mass, total cannabis plant weight, days to first flower, number of fruits, weight of fruits, mean fruit weight, number of seeds, weight of seeds, mean seed weight, tuber weight, tuber diameter, leaf size, leaf weight, leaf length, leaf width, leaf area, number of leaves, stem length, stem weight, stem. diameter, number of petioles, length of petioles, number of ovaries, pollen amount, pollen size, standability, resistance to lodging, disease resistance, disease avoidance, cold hardiness, heat tolerance, drought tolerance, days to maturity, days to pollen release, color, emergence, rate of photosynthesis, number of nodes, length of node, number of lateral roots, length of primary root, number of stomata, density of stomata, number of stolans, stolan length, number of rhizomes, rhizome length, and harvestability. In some embodiments, weight of a cannabis plant or a cannabis plant part refers to fresh weight or dried weight.

As used herein, the term "active polymer" refers to a system comprising one or more types of minerals and a polymer matrix wherein said mineral particles are suspended, embedded, or otherwise incorporated in said polymer matrix. The active polymer is capable of harvesting photon energy. The active polymer will be described in greater detail elsewhere herein. For the purposes of this application, the terms "active polymer" and "active polymer material" are used interchangeably.

As used herein, the phrase "harvest photon energy" refers to the act of absorbing photons whereby a molecule or atom comprising the material absorbing the photon transitions from the ground state to the excited state. Photons are particles representing quantum units of light, both visible and invisible to the naked eye, and carrying energy proportional to the electromagnetic radiation frequency.

As used herein, the term "absorption" refers to the physical process of absorbing light and term "absorbance" refers to a mathematical quantity expressing the ratio of light or radiation that falls upon a material and the amount that gets transmitted through the material.

As used herein, the term "absorptivity" and "absorbance" refers to the optical absorption properties exhibited by a material.

As used herein, the term "transmission of light" refers to the light that is passed through a material without being absorbed. As used herein, the term "transmissivity" and "transmittance" refers to the optical transmission properties exhibited by a material.

As used herein, the term "reflection" refers to the light that bounces back upon hitting a material or the light and its energy that is re-emitted upon hitting a material. As used herein, the term "reflectivity" or "reflectance" refers to the optical reflection properties exhibited by a material.

As used herein, the term "refraction" refers to a change in the transmitted light direction due to change in the transmission medium such as water or glass.

As used herein, the term "polarize" refers to the physical process in which light or radiation reflects off of or partially passes through a particle or a material where the direction of electric and magnetic field vectors in the wave is altered. Polarization of light or radiation may be partial or complete.

As used herein, the terms "emit light," "emitting light," or "emission of light" each refer to the physical process in which the excited state of the molecule or an atom due to absorption of energy falls back to its ground state thereby releasing energy in the form that can be quantified by its wavelength or a range of wavelengths. As used herein, the terms "emissivity" or "emittance" each refer to the optical emission properties exhibited by a material.

It is noted that the National institute of Standards and Technology (NIST) has recommended to reserve the ending "-ivity" (such as in reflectivity and transmissivity) for radiative properties of pure, perfectly smooth materials and using the ending "-ance" (such as in reflectance and transmittance) for rough and contaminated surfaces.

As used herein, the term "light scattering" refers to a physical process in which light is reflected off of an object in many different directions due to the irregularities of the hitting surface or when hitting interfering particles, that is in between the object and the source of light. Small particles suspended in air can cause light scattering.

As used herein, the term "refractive index" refers to the ability of a particular substance to bend light when light is entering said substance.

As used herein, the term "extrude" refers to a process in which a material is forced out through a die to form material into certain shapes.

As used herein, the term "fiber" refers to an elongated, thread-like structured material having a characteristic longitudinal dimension (length) and a characteristic transverse dimension (diameter), wherein fibers can be used as component of a composite material by weaving or stitching. Fibers can be short (discontinuous) or long (continuous).

As used herein, the term "denier" refers to a unit of measure for the linear mass density of fibers. For example, a fiber having a length of 9000 m and weighing 1 gram has a denier of 1 (aka 1-denier).

As used herein, the term "staple fiber" refers to a short or discontinuous fiber where the length of the fiber is cut in the length approximately from about 0.1 cm to about 15 cm.

As used herein, the term "film" refers to a flat or tubular flexible structure of the material used.

As used herein, the term "mesh" refers to a composition constructed of a material having the appearance of a net (e.g., with holes, or pores).

As used herein, the term "batting material" refers to a material made of a soft, bulky assembly of non-woven fibers or foam.

As used herein, the term "die-cut" refers to a process in which fiber, textile, or material is cut into shapes using a die.

As used herein, the term "growth media," "growing media," or "*cannabis* plant growth media" refers to various natural and artificial media which support *cannabis* plant growth. Non-limiting examples include natural or artificial soil, peat moss, sand, clay, pumice, organic mulch, rock, wool, rockwool, vermiculite, growstones, coir, rice hulls, perlite, gravel, wood fiber, sheep wool, brick shards, polystyrene packing peanuts, natural and synthetic fibers, potting mixtures of organic and inorganic matter, artificial media such as polyurethane foam, and the like.

As used herein, the term "kit" refers to components intended for use together. An indication that components of a kit are for use together can be, for example, packaging of the components in a single package, or labeling either or both of the components as being for use in combination, or both.

As used herein, the term "Celliant™" refers to a patented material and technology described by U.S. Pat. No. 7,074,499. Celliant is a bi-component material comprising of thermo-reactive particles which are embedded into fibers. Textile made from Celliant fiber is shown to effectively convert body heat into medically useful infrared radiation. Therapeutic values of infrared radiation include promotion of blood circulation and increase in oxygen level in the blood stream. In some embodiments Celliant comprises 55% SiC, 25% $TiO_2$, 5% $SiO_2$, and 15% $Al_2O_3$ minerals composition.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated for all purposes by reference in their entirety.

Cannabis

*Cannabis*, more commonly known as marijuana, is a genus of flowering plants that includes at least three species, *Cannabis sativa, Cannabis indica*, and *Cannabis ruderalis* as determined by plant phenotypes and secondary metabolite profiles. In practice however, *cannabis* nomenclature is often used incorrectly or interchangeably. *Cannabis* literature can be found referring to all *cannabis* varieties as "sativas" or all cannabinoid producing plants as "indicas". Indeed the promiscuous crosses of indoor *cannabis* breeding programs have made it difficult to distinguish varieties, with most *cannabis* being sold in the United States having features of both *sativa* and indica species.

*Cannabis* is one of the world's oldest and most useful cultivated genus of plants. Humans have used hemp varieties of *cannabis* for the production of industrial materials, including food, paper, textiles, plastics, detergents, and biofuels. Humans also have a long history of using psychoactive varieties of *cannabis* for medical and recreational applications. *Cannabis* has long been used for drug and industrial purposes, fiber (hemp), for seed and seed oils, for medicinal purposes, and as a recreational drug. Industrial hemp products are made from *Cannabis* plants selected to produce an abundance of fiber. Some *Cannabis* strains have been bred to produce minimal levels of THC, the principal psychoactive constituent responsible for the psychoactivity associated with marijuana. Marijuana has historically consisted of the dried flowers of *Cannabis* plants selectively bred to produce high levels of THC and other psychoactive cannabinoids. Various extracts including hashish and hash oil are also produced from the plant.

Interest in psychoactive varieties of *cannabis* has recently exploded following the relaxation drug laws within the United States, and with the discovery of previously unrecognized applications for *cannabis* in the treatment of human diseases such as diabetes, epilepsy, schizophrenia, and cancer.

*Cannabis* is diploid, having a chromosome complement of $2n=20$, although polyploid individuals have been artificially produced. The first genome sequence of *Cannabis*, which is estimated to be 820 Mb in size, was published in 2011 by a team of Canadian scientists (Bakel et al, "The draft genome and transcriptome of *Cannabis sativa*" Genome Biology 12:R102).

All known strains of *Cannabis* are wind-pollinated and the fruit is an achene. Most strains of *Cannabis* are short day plants, with the possible exception of *C. sativa* subsp. *sativa* var. spontanea (=*C. ruderalis*), which is commonly described as "auto-flowering" and may be day-neutral.

The genus *Cannabis* was formerly placed in the Nettle (Urticaceae) or Mulberry (Moraceae) family, and later, along with the *Humulus* genus (hops), in a separate family, the Hemp family (Cannabaceae sensu stricto).http://en.wikipedia.org/wiki/*Cannabis*-cite_note-schultes2001a-21 Recent phylogenetic studies based on cpDNA restriction site analysis and gene sequencing strongly suggest that the Cannabaceae sensu stricto arose from within the former Celtidaceae family, and that the two families should be merged to form a single monophyletic family, the Cannabaceae sensu lato.

*Cannabis* plants produce a unique family of terpenophenolic compounds called cannabinoids. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. There are at least 483 identifiable chemical constituents known to exist in the *cannabis* plant (Rudolf Brenneisen, 2007, Chemistry and Analysis of Phytocannabinoids (cannabinoids produced by *cannabis*) and other *Cannabis* Constituents, In Marijuana and the Cannabinoids, ElSohly, ed.; incorporated herein by reference) and at least 85 different cannabinoids have been isolated from the plant (El-Alfy, Abir T, et al., 2010, "Antidepressant-like effect of delta-9-tetrahydrocannabinol and other cannabinoids isolated from *Cannabis sativa* L", Pharmacology Biochemistry and Behavior 95 (4): 434-42; incorporated herein by reference).http://en.wikipedia.org/wiki/*Cannabis*-cite_note-26 The two cannabinoids usually produced in greatest abundance are cannabidiol (CBD) and/or $\Delta^9$-tetrahydrocannabinol (THC). THC is psychoactive while CBD is not. See, ElSohly, ed. (Marijuana and the Cannabinoids, Humana Press Inc., 321 papers, 2007), which is incorporated herein by reference in its entirety, for a detailed description and literature review on the cannabinoids found in marijuana.

Cannabinoids are the most studied group of secondary metabolites in *cannabis*. Most exist in two forms, as acids and in neutral (decarboxylated) forms. The acid form is designated by an "A" at the end of its acronym (i.e. THCA). The phytocannabinoids are synthesized in the plant as acid forms, and while some decarboxylation does occur in the plant, it increases significantly post-harvest and the kinetics increase at high temperatures. (Sanchez and Verpoorte 2008). The biologically active forms for human consumption are the neutral forms. Decarboxylation is usually achieved by thorough drying of the plant material followed by heating it, often by either combustion, vaporization, or heating or baking in an oven. Unless otherwise noted, references to cannabinoids in a plant include both the acidic and decarboxylated versions (e.g., CBD and CBDA).

The cannabinoids in *cannabis* plants include, but are not limited to, $\Delta^9$-Tetrahydrocannabinol ($\Delta^9$-THC), $\Delta^8$-Tetrahydrocannabinol ($\Delta^8$-THC), Cannabichromene (CBC), Cannabicyclol (CBL), Cannabidiol (CBD), Cannabielsoin (CBE), Cannabigerol (CBG), Cannabinidiol (CBND), Cannabinol (CBN), Cannabitriol (CBT), and their propyl homologs, including, but are not limited to cannabidivarin (CBDV), $\Delta^9$-Tetrahydrocannabivarin (THCV), cannabichromevarin (CBCV), and cannabigerovarin (CBGV). See Holley et al. (Constituents of *Cannabis sativa* L. XI Cannabidiol and cannabichromene in samples of known geographical origin, *J. Pharm. Sci.* 64:892-894, 1975) and De Zeeuw et al. (Cannabinoids with a propyl side chain in *Cannabis*, Occurrence and chromatographic behavior, Science 175:778-779), each of which is herein incorporated by reference in its entirety for all purposes. Non-THC cannabinoids can be collectively referred to as "CBs", wherein CBs can be one of THCV, CBDV, CBGV, CBCV, CBD, CBC, CBE, CBG, CBN, CBND, and CBT cannabinoids.

In addition to cannabinoids, *cannabis* also produces over 120 different terpenes (Russo 2011, Taming THC: potential *cannabis* synergy and phytocannabinoid-terpenoid entourage effects, *British Journal of Pharmacology*, 163:1344-1364). Within the context and verbiage of this document the terms 'terpenoid' and 'terpene' are used interchangeably. Examples of representative terpines include, but are not limited to, terpinolene, alpha phelladrene, beta ocimene, carene, limonene, gamma terpinene, alpha pinene, alpha terpinene, beta pinene, fenchol, camphene, alpha terpineol, alpha humulene, beta caryophyllene, linalool, cary oxide, and myrcene.

Cannabinoids are odorless, so terpenoids are responsible for the unique odor of *cannabis*, and each variety has a slightly different profile that can potentially be used as a tool for identification of different varieties or geographical origins of samples (Hillig 2004. "A chemotaxonomic analysis of terpenoid variation in *Cannabis*" Biochem System and Ecology 875-891). It also provides a unique and complex flavor smell, and effect profile for each variety that is appreciated by both novice users and connoisseurs. In addition to many circulatory and muscular effects, some terpenes interact with neurological receptors. A few terpenes produced by *cannabis* plants also bind weakly to Cannabinoid receptors. Some terpenes can alter the permeability of cell membranes and allow in either more or less THC, while other terpenes can affect serotonin and dopamine chemistry as neurotransmitters. Terpenoids are lipophilic, and can interact with lipid membranes, ion channels, a variety of different receptors (including both G-protein coupled odorant and neurotransmitter receptors), and enzymes. Some are capable of absorption through human skin and passing the blood brain barrier.

*Cannabis* is an annual, dioecious, flowering herb. The leaves are palmately compound or digitate, with serrate leaflets. *Cannabis* normally has imperfect flowers, with staminate "male" and pistillate "female" flowers occurring on separate plants. It is not unusual, however, for individual plants to separately bear both male and female flowers (i.e., have monoecious plants). Although monoecious plants are often referred to as "hermaphrodites," true hermaphrodites (which are less common in *cannabis*) bear staminate and pistillate structures on individual flowers, whereas monoecious plants bear male and female flowers at different locations on the same plant.

The life cycle of *cannabis* varies with each variety but can be generally summarized into germination (or rooting/recovery after asexual propagation), vegetative growth, and reproductive stages. Because of heavy breeding and selection by humans, most *cannabis* seeds have lost dormancy mechanisms and do not require any pre-treatments or winterization to induce germination (See Clarke, R C et al. "*Cannabis*: Evolution and Ethnobotany" University of California Press 2013). Seeds placed in viable growth conditions are expected to germinate in about 3 to 7 days. The first true leaves of a *cannabis* plant contain a single leaflet, with subsequent leaves developing in opposite formation. In some embodiments, subsequent leaves develop with increasing number of leaflets. Leaflets can be narrow or broad depending on the morphology of the plant grown. *Cannabis* plants are normally allowed to grow vegetatively for the first 4 to 8 weeks. During this period, the plant responds to increasing light with faster and faster growth. Under ideal conditions, *cannabis* plants can grow up to 2.5 inches a day, and are capable of reaching heights of up to 20 feet. Indoor growth pruning techniques tend to limit *cannabis* size through careful pruning of apical or side shoots.

Although, some *cannabis* varieties will flower without the need for external stimuli, most varieties have an absolute requirement for inductive photoperiods in the form of short days or long nights to induce fertile flowering. The first sign of flowering in *cannabis* is the appearance of undifferentiated flower primordial along the main stem of the nodes. At this stage, the sex of the plants are still not distinguishable. As the flower primordia continue to develop, female (pistillate), and male (staminate) flowers can be distinguished.

For most cannabinoid producing purposes, only female plants are desired. The presence of male flowers is considered undesirable as pollination is known to reduce the cannabinoid yield, and potentially ruin a crop. For this reason, most *cannabis* is grown "sinsemilla" through vegetative (i.e., asexual) propagation. In this way, only female plants are produced and no space is wasted on male plants.

Commercial production of these medicinal and recreational *cannabis* varieties however, has been slowed down by the lack of true-breeding psychoactive genetics. Indeed, most popular *cannabis* strains in the market do not have fixed genetics, and are unable to produce uniform progeny when propagated through seeds. Modern *cannabis* production techniques thus rely on asexual cuttings of single *cannabis* "mother" plants to produce uniform crops of genetically identical plants. Current asexual reproduction techniques however, still represent a major bottleneck in *cannabis* production yields. Improper techniques and incorrect hormones and nutrient formulations result in low propagation yields, and slow rooting and recovery of successful clones. Although asexual reproduction of *cannabis* is somewhat easily performed, its inherent constraints of time, space and resources severely limits the total number of plants that can be produced in large scale commercial operations. Furthermore, asexual reproduction of *cannabis* is constantly plagued by a host of other problems, including, but not limited to, abiotic disorders (e.g., nutrition, light quality and quantity, water availability, etc.); pathogens (e.g., Powdery Mildew and *Pythium* root rots); mites (e.g., two spotted spider mites and hemp russet mite); aphids (e.g., rice root aphid and hop aphid); white flies; viruses (e.g., Tobacco Mosaic Virus) and fungus gnats.

The present disclosure generally relates to compositions, systems, and methods for growing *Cannabis* tissues, plant parts and whole plants. The disclosures of the present invention circumvent many of the problems associated with the large or mass scale production of *cannabis*.

The compositions, systems and methods of the present invention can be used for the growing and production of any *Cannabis* germplasm. Around one-fifth of Americans now live in states where marijuana is legal for adult use, according to the Brookings Institution, and an estimated 200 million live in places where medicinal marijuana is legal. *Cannabis* germplasms, strains, varieties and/or lines are now publicly and commercially available in many states. U.S. Pat. No. 6,630,507 issued on Oct. 7, 2003 and assigned on the patent face to The United States of America, is directed to methods of treating diseases caused by oxidative stress by administering therapeutically effective amounts of a cannabidiol (CBD) cannabinoid from *cannabis* plants that has substantially no binding to the N-methyl-D-aspartate (NMDA) receptor, wherein the CBD acts as an antioxidant and neuroprotectant. A search of the U.S.P.T.O Patent Application Information Retrieval (PAIR) system also reveals the existence of thousands of *cannabis*-related applications and issued patents including U.S. Pat. No. 8,034,843 (use of cannabinoids for treating nausea, vomiting, emesis, motion sickness), U.S. Pat. No. 7,698,594 (cannabinoid compositions for treatment of pain), and U.S. Pat. No. 8,632,825 (anti-tumoural effects of cannabinoid combinations) among many others. Some examples of publicly-disclosed *Cannabis* germplasms, strains, varieties and/or lines each of which produce different amounts and/or ratios of *cannabis* metabolites can be found, e.g., in U.S. Pat. Nos. 9,095,554; 9,370,164; and 9,642,317; and U.S. Published Patent Application Nos. 20110098348; 20140287068; 20160324091; and 20160360721, each of which is specifically incorporated by reference herein in its entireties, including all of the tables and figures. Specific strains of *cannabis* are disclosed in U.S. Published Patent Application Nos. 20140245494 and 20160073567 ('*Cannabis* Plant Named Erez'); 20140245495 20160073568 ('*Cannabis* Plant Named Midnight'); 20140259228 and 20160073566 ('*Cannabis* Plant Named Avidekel'); 20160000843 ('High Cannabinol *Cannabis* Strains'); 20160345477 ('*Cannabis* Plant Named Ecuadorian *Sativa*'); and 20170172040 ('*Cannabis* Plant Named Katelyn Faith').

*Cannabis* Plants and Electromagnetic Radiation

The sun produces electromagnetic radiation over a broad spectrum including ultraviolet light, visible light, and infrared light. Ultraviolet (UV) light has wavelengths from about 10 nm to about 390 nm which can be further subdivided into far (10 to 200 nm), mid (200 to 300 nm), and near (300 to 390 nm) spectra regions. Next to the UV light region is the visible light region which carries less energy than UV light. Visible light is only a small band in the electromagnetic spectrum with wavelengths between about 390 nm and about 770 nm, which are further divided into violet (390-450 nm), blue (450-495 nm), green (495-570 nm), yellow (570-590 nm), orange (590-620 nm), and red light (620-770 nm). Infrared (1R) light, even less energy than the visible light, spans from about 770 nm to about 1060 gm and includes near (770 to 1500 nm), mid (1500 nm to 6 gm) and far (6 to 1060 gm) regions.

*Cannabis* plants depend on energy from the sun to grow. Photosynthesis is a well-known chemical reaction by which electromagnetic radiation is absorbed through chlorophyll pigments to trigger electron transport chains, and ultimately lead to the production of chemical energy stored in the form of proteins, sugars, and oils. This process however only utilizes a small portion of the solar radiation.

Photosynthesis typically only occurs with visible light in the range of about 400 nm to 700 nm, which makes up about 42% of the total solar radiation energy. Even within this narrow range, light absorption by the chlorophyll pigments of green *cannabis* plants is further focused on the 430 nm (blue) and 670 nm (red) regions of the spectrum. (Singhal, G. S. et. al. "Concepts in Photobiology: Photosynthesis and Photomorphogenesis" Eds. 1999, Kluwer Academic Publishers). Thus photosynthesis, while critical to *cannabis* plant growth only utilizes a small portion of the electromagnetic radiation emitted by the sun.

Other portions of the light spectrum can affect *cannabis* plant growth and development in other ways. For example, *cannabis* plants have evolved light receptors which allow them. To "sense" their environments and respond to changing conditions (Photomorphogenesis, Singhal, G. S. et. al. "Concepts in Photobiology: Photosynthesis and Photom.orphogenesis" Eds. 1999, Kluwer Academic Publishers). Changes in light intensities, periods, and wavelengths can have profound effects on *cannabis* plant morphologies ranging from germination, flowering times, shade avoidance, vegetative growth, anthocyanin accumulation, and stomatal openings (Wang et al. Contributions of green light to *cannabis* plant growth and development" Am. J. Botany 2013, 1, 70-78). Furthermore, each *cannabis* plant's response to various light cues will depend on the species, growth stage, and geographical acclimation of said *cannabis* plant. For example, the germination of certain species is triggered by red light, while the germination of other species is triggered by blue light, or a combination of blue or red light with green light (Wang et al. "Contributions of green light to *cannabis* plant growth and development" Am. J. Botany 2013, 1, 70-78).

Another important role of solar radiation is its ability to produce heat. IR radiation accounts for almost half of the solar radiation reaching the earth (about 49%). This IR portion of the spectrum is readily absorbed by water and carbon dioxide molecules which in turn convert that energy into heat released into the environment. By affecting the temperature of soils and *cannabis* plants, IR light can influence the growth and development of *cannabis* plants ("Soil Temperature and *Cannabis* Plant Growth in the Northern Great Plains" Willis, W. 0 et al. Prairie: A Multiple View: 1975, University of North Dakota Press, Grand Forks, Wali, Mohan K. Ed.). Indeed soil temperature can have profound effects on the timing and speed of *cannabis* plant seed germinations (Roberts E H et al., "Temperature and Seed Germination." Sympo Soc Exp Biol 1988; 42:109-32). IR radiation has also been found to increase microbial activity and result in favorable conditions for *cannabis* plant growth such as faster breakdown of nutrients by microbes (Nature 2006, 440, 165-173).

*Cannabis* Plants themselves may also use solar radiation for their own purposes. By carefully controlling the spectrum of reflected light, *cannabis* plants have evolved visual cues to discourage potential predators (e.g., herbivores), and attract desired pollinators (e.g., insects and birds) (Lunau, K. et. al. "Innate Colour Preferences of Flower Visitors" J. Comp. Physiol. A 1995, 177, 1-19). In some cases, the reflective properties of a flower have evolved such that the reflected spectrum is only visible to selected organisms (Vignolini et al. 2014, "The flower of Hibiscus trionum is both visibly and measurably iridescent." New Phytol July 16).

Solar radiation outside of the visible light range can also be harmful to *cannabis* plants, especially when shined in excess. UV light constitutes only about 8% of total solar radiation, but can cause serious damages to *cannabis* plant DNA, proteins, and membranes (U-V-B light 280-315 nm) (Trends in *Cannabis* Plant Science 1998, 3, 131-135). UV-B light is present even if the sunlight is mostly blocked by the clouds on an overcast day. The ratio of UV-B light and visible light is also important in protecting the *cannabis* plants from UV-B damage. Thus, consecutive cloudy days may be damaging to *cannabis* plants because the ratio of UV-B to visible light is high (*Cannabis* Plant, Cell & Environment 1994, 17, 295-301).

Optimizing *Cannabis* Plant Growth Through Light Manipulation

The manipulation of light to optimize *cannabis* plant growth has been a goal of growers for many years. One type of light manipulation has been the attenuation of light intensity through the use of shade coverings (Ghosal et al. 2003. "Modeling and experimental validation of a greenhouse with evaporative cooling by moving water film, over external shade cloth" Energy and Buildings Vol 35:8 pg 843-850). Other attempts at using colored materials have led to limited control of visible spectrums through coverings or nettings (Al-Fielal, I. M. et. al. "Measuring and Evaluating Solar Radiative Properties of Plastic Shading Nets" 2011, 95, 677-683).

Perhaps one of the most obvious examples of light manipulation has been the use of greenhouses for indoor *cannabis* plant cultivation. Greenhouses are traditionally built to retain the effects of IR radiation, while also using glass panels to filter out harmful UV spectrums. Modern greenhouses are also equipped with sophisticated shading and lighting systems to supplement for reduced solar radiation, or protect *cannabis* plants from excess exposure.

More recently, the use of custom light emitting diode lamps (LEDs) have allowed researchers to carefully tailor light profiles to meet individual *cannabis* plant's needs in laboratory settings and limited greenhouse settings. For example, in a particular experiment, increased levels of blue light were found to stunt strawberry *cannabis* plant elongation, while increased red light was found to increase *cannabis* plant height and flowering rate (Folta et al., 2008 "Light as a Growth Regulator: Controlling *Cannabis* Plant Biology with Narrow-bandwidth Solid-state Lighting Systems" HortScience 2008, 7, 1951-1956).

Another example of light manipulation to regulate *cannabis* plant growth is the use of polarized light. Polarization refers to the physical process in which the direction of light wave vibration is altered. Solar radiation is not polarized as it shines onto the Earth. Non-polarized light from the sun thus exhibits wave vibrations in all directions. Polarizers are materials that filter specific directions of wave vibration, only allowing single direction wave orientations to pass through. One of the most familiar examples of this phenomenon is the production of polarized sunglasses which can be designed to reduce light reflections with certain wave orientations. Certain polarizers, such as a circular polarizer, have been shown to affect *cannabis* plant growth when the polarized light is absorbed by the interior of the leaves or the stems (Shibayev, P. P. et. al. "The Effect of Circularly Polarized Light on the Growth of *Cannabis* Plants" Int. J. Botany 2011, 7, 113-117).

These experiments, while key for developing the concepts of dynamic light manipulation, are not practical for consumer application. The equipment and energy costs associated with LED lighting make efforts to provide artificial lighting at a large scale very expensive if not cost-prohibitive. Similarly, the indiscriminate use of polarizing filters can significantly reduce light intensity and lead to undesirable *cannabis* plant morphologies. Finally, the above described laboratory approaches only accounted for the use of light as a biological signal, and did not include teachings of the outdoor manipulation of the effects of IR heating, or the selective mitigation of UV radiation. Furthermore, current limiting applications of LED lighting for the use in greenhouses have excluded far IR considerations as an effective wavelength use.

Thus there still exists a need for alternative methods to manipulate light spectra in commercial greenhouse and field settings.

Active Polymer Material

The present disclosure addresses the challenges associated with harvesting solar energy and effectively utilizing it for *cannabis* plant growth. The present disclosure is based in part on the inventors' discovery that active polymer materials (APM) can be produced to create custom light reflection and absorption profiles designed to enhance *cannabis* plant growth and/or direct *cannabis* plant development. The present disclosure teaches APM compositions, and methods for producing and using said APMs.

In some embodiments, APMs comprise at least one type of mineral and a polymer matrix, wherein the mineral is suspended, embedded or otherwise incorporated in the polymer matrix. In some embodiments, the active polymer material is capable of absorbing photon energy in the electromagnetic light spectrum and shifting the wavelength of light to another desired portion of the spectrum. In other embodiments, the active polymer material interacts with electromagnetic light by absorbing, reflecting, refracting, polarizing and/or shifting the wavelength. Thus in some embodiments the APM combines the mineral and polymer components to create custom light absorption and reflective profiles.

Mineral Used in the Active Polymer Material

In some embodiments, the active polymer material comprises at least one type of mineral. Said mineral is selected based upon several characteristics. In some embodiments, mineral of the present invention are biologically benign, or inert. In other embodiments, said mineral exhibits optical properties of being transparent or semi-transparent.

Fluorescence

In some embodiments, the mineral of the present invention is chosen for its ability to fluoresce. For example, in some embodiments, the present invention teaches the use of minerals such as calcites and ambers which fluoresce under UV light in various colors of the visible range. Thus in some embodiments, the minerals of the present invention absorb radiation in the UV spectrum, not visible to human eyes, and release said energy in the form of light in the visible light range. For representative examples of UV shifting minerals, see EP 0579835, U.S. Pat. No. 5,958,294, and Chinese Pat. App. No. 103,224,660.

In some embodiments, the mineral of the present invention comprise one or more compounds of the general descriptor $X_mY_n$, wherein X does not equal Y (e.g., $X \neq Y$), one or more elements can be selected to form X, one or more elements can be selected to form Y, and m and n are greater than or equal to 1 and less than or equal to 100, independently (111100 and 111.100). The elements that make up the compositions of X and Y are independently selected from the group consisting of hydrogen (H), lithium (Li), beryllium (Be), sodium (Na), magnesium (Mg), potassium (K), calcium (Ca), rubidium (Rb), strontium (Sr), cesium (Cs), barium (Ba), francium (Fr), radium (Ra), scandium (Sc), titanium go, vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), lutetium (Lu), hafnium (HO), tantalum (Ta), tungsten (W,) rhenium (Re), osmium (Os), iridium (Ir), platinum (Pt), gold (Au), mercury (Hg), lawrencium (Lr), rutherfordiurn (RO), dubniurn (Db), seaborgium (Sg), bohriurn (Bh), hassium (Hs), meitneriurn (Mt), darmstadtium (Ds), randon (Rn), indium (In), boron (B), carbon (C), nitrogen (N), oxygen (O), fluorine (F), aluminum (Al), silicon (Si), phosphorus (P), sulfur (S), chlorine (Cl), gallium (Ga), germanium (Ge), arsenic (As), selenium (Se), bromine (Br), indium (In), tin (Sn), antimony (Sb), tellurium (re), iodine (I), lead (Pb), bismuth (Bi), polonium (Po), astatine (At), ununtrium (Uut), thallium (Ti), ununpentium (pup), lutetium (Lu), ununseptium (Uus), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), yitterbium (Yb), actinium (Ac), thorium (Th), protactinium (Pa), uranium (U), *neptunium* (Np), plutonium (Pu), americium (Am), curium (Cm), berkelium (Bk), californium (CO, einsteinium (Es), fermium (Fm), mendelevium (Md), and nobelium (No).

In some embodiments, the mineral comprises one type of mineral compound.

In other embodiments, the mineral comprises one or more types of mineral compounds. Thus in some embodiments the mineral may comprise $X_mY_nZ_o$, formula, where X, Y and Z each represent an element or a mineral compound and m, n and o represent the relative ratios of their respective elements or mineral compounds. In other embodiments, the mineral may comprise $X_mY_nZ_oW_p$ formula, where X, Y, Z, and W each represent an element or a mineral compound and m, n, o, and p represent the relative ratios of their respective elements.

In some embodiments, X, Y, Z, and W in the mineral composition of $X_mY_nZ_oW_p$, is each selected from the group consisting of Si, Ti, Al, Ca, Na, Cu C, O, N, and S.

In other embodiments, one or more minerals in the active polymer material are selected from the group consisting of silicon carbide (SiC), calcium carbide (CaC2), titanium. dioxide (TiO2), aluminum oxide (A1203), and silicon dioxide (SiO2).

In some embodiments, the minerals in the active polymer material comprise SiC, TiO2, SiO2, and A1203.

Mineral Size and Shape

In some embodiments, the mineral particles of the present invention are processed into certain sizes or shapes to alter their optical properties. In some embodiments, the mineral particles are reduced in size and shape by a process known in the art, such as grinding, polishing, or tumbling. These processes help to determine the particle size of the mineral, the concentration of each type of minerals, and the physical characteristics of the mineral. The physical characteristics may include the smoothness and/or shape of the mineral particles.

In some embodiments, the mineral particles are reduced in size to a substantially scalloped shape. Said substantially scalloped shaped mineral particles may shift wavelengths of received light. In other embodiments, the mineral particles are reduced in size to substantially spherical shape. Said substantially spherical shaped mineral particles may shorten wavelength of the received light. In other embodiments, the mineral particles are reduced in size to substantially triangular shape with round edges. Said substantially triangular shaped mineral particles with round edges may reflect, absorb, or scatter the received light. In other embodiments, the mineral particles are reduced in size to substantially convex shape. While not wishing to be bound to any particular theory, we believe said substantially convex shaped mineral particles allow for maximum surface area to interact with light.

In some embodiments, the average mineral particle size is about 0.5 to about 2.0 microns. That is, the mineral particle may have an average size of about 0.50 microns, 0.55 microns, 0.60 microns, 0.65 microns, 0.70 microns, 0.75 microns, 0.80 microns, 0.85 microns, 0.90 microns, 0.95 microns, 1.00 microns, 1.05 microns, 1.10 microns, 1.15 microns, 1.20 microns, 1.25 microns, 1.30 microns, 1.35 microns, 1.40 microns, 1.45 microns, 1.50 microns, 1.55 microns, 1.55 microns, 1.60 microns, 1.65 microns, 1.70 microns, 1.75 microns, 1.80 microns, 1.85 microns, 1.90 microns, 1.95 microns, or 2.00 microns.

In some embodiments, the average mineral particle size is about 0.5 to about 2.0 microns. That is, the mineral particle may have an average size is in the range of about 0.50-0.60 microns, 0.60-0.70 microns, 0.70-0.80 microns, 0.80-0.90 microns, 0.90-1.00 microns, 1.00-1.10 microns, 1.10-1.20 microns, 1.20-1.30 microns, 1.30-1.40 microns, 1.40-1.50 microns, 1.50-1.60 microns, 1.60-1.70 microns, 1.70-1.80 microns, 1.80-1.90 microns, and 1.90-2.00 microns.

In some embodiments, the mineral particle size may be related to the target wavelength of its absorption. For example, if the target absorption is about 750 nm, then the mineral particle may be reduced to a size of about 750 nm.

In some embodiments, the mineral particles may be ground to reach an approximate particle size of about 0.5 microns to about 2.0 microns. For example, titanium dioxide may be ground to a grain size of between about 1 micron and about 2 microns and may be triangular with rounded edges. Aluminum oxide may be ground to a grain size of between about 1 and about 1.5 microns and may be scalloped-shaped. Silicon dioxide may be ground to a gain size of about 1 to about 1.5 microns and is generally rounded.

In some embodiments, the present invention teaches a dry weight ratio of the active materials of 55% SiC, 25% $TiO_2$, 5% $SiO_2$, and 15% $Al_2O_3$.

Polymer Matrix

In some embodiments, the minerals of the APMs are embedded within a polymer matrix. In some embodiments, the polymers for the APMs are chosen for their ability to hold the mineral particles. In other embodiments, the polymers for the APMs are chosen so that the mineral and the polymer matrix do not chemically react.

In other embodiments, the polymers of the APMs are chosen for their ability to be shaped or manufactured for particular uses. Some polymers are flexible and can be manipulated and re-shaped multiple ti.m.es. For example, polyethylene terephthalate (PET) is a thermally induced shape-memory polymer that can lose its form at high temperatures, and be reformed into useful shapes.

In some embodiments, the polymers of the APMs are chosen for their compatibility with the environment. For example, soil covers made from polymer carbohydrates and vegetable fillers are known to be biodegradable (see for example U.S. Pat. No. 5,879,695). In another example, a soil cover made of polyethylene polymer fibers are durable yet photodegradable and slowly degrades when used outdoors (U.S. Pat. No. 5,532,298). In some embodiments, the APMs can be formed into useful materials such as fibers and films based on the properties of the polymer matrix used.

In other embodiments, the polymers of the present invention are selected based on their ability to interact with light radiation by absorbing, reflecting, refracting, and/or changing the wavelength. In some embodiments, PET polymers are effective in polarizing solar radiation.

In some embodiments, the polymer matrix of the present invention may be selected from a group consisting of rayon, acrylonitrile butadiene styrene, acrylic, celluloid, cellulose acetate, cycloolefin copolymer, ethylene-vinyl acetate, ethylene vinyl alcohol, fluoroplastics, ionomers, KYDEXO, liquid crystal polymer, polyacetal, polyacrylates, polyacrylonitrile, polyamide, polyamide-imide, polyaryletherketone, polybutadiene, polybutylene, polybutylene terephthalate, polycaprolactone, polychlorotrifluoroethylene, polyethylene terephthalate, polycyclohexylene dimethylene terephthalate, polycarbonate, polyhydroxyalkanoates, polyketone, polyester, polyethylene, polyetheretherketone, polyetherketoneketone, polyetherimide, polyethersulfone, polyethylenechlorinates, polyimide, polylactic acid, polymethylpentene, polyphenylene oxide, polyphenylene sulfide, polyphthalamide, polystyrene, polysulfone, polytrimethylene terephthalate, polyurethane, polyvinyl acetate, polyvinyl chloride, polyvinylidene chloride, and styrene-acrylonitrile.

In some embodiments, the polymer matrix comprises one type of a polymer. In other embodiments, the polymer matrix comprises one or more types of polymers.

In some embodiments, the APM comprises one or more polymers that have a polarizing filter. In some embodiments, the APM comprises one or more polymer types selected from the group consisting of polyethylene terephthalate (PET), polyester, nylon, rayon, and spandex. In some embodiments, the polymer matrix is PET.

In some embodiments, the polymer matrix may contain additives such as coloring agent, surface stabilizer, surfactants, UV stabilizers, plasticizers, slip agents, mineral fillers, bonding agents, antistatic agents, oils, antioxidants, adhesives, and the like. In some embodiments the coloring agent affects the optical properties of said polymer.

For additional information on the active polymeric material see U.S. Pat. No. 7,074,499 (Polymeric Fiber Composition and Method), which is incorporated herein in its entirety.

Properties of Active Polymer Material

In some embodiments, the APM may absorb a light wave and emit a different wave. Thus in some embodiments, the APM may shorten the wavelength of the absorbed light. In other embodiments, the APM may lengthen the wavelength of the absorbed light, depending on the desired effect. In yet other embodiments the APM of the present invention may be designed to absorb a portion of the light spectrum and convert it to heat or other type of energy. In some embodiments the APM of the present invention may allow for the transmission of portions of the spectrum such that selected wavelengths are allowed to pass through the APM. In other embodiments the APM of the present invention may reflect selected portions of the light spectrum. In yet other embodiments, the APM may be designed to selectively polarize certain portions of the spectrum, either during transmission, or reflection of said waves.

In some embodiments, a combination of the mineral and the polymer matrix may result in the APM that emits light at a specific range. For example, in some embodiments, aluminum oxide promotes IR light lengthening. When said APM comprising aluminum oxide interacts with IR light, in some embodiments, the material releases light in a longer IR range than the range it absorbed.

Similarly, silicon dioxide has a unique property of interacting with UV light when combined with certain polymer matrices. In some embodiments, an APM comprising silicon dioxide may absorb one range of UV light but emit light in shorter wavelengths.

In some embodiments, when more than one type of mineral is used to construct the APM, the material may exhibit synergistic optical properties of those different minerals.

In some embodiments, the mineral particles and the polymer matrix, independently, may have a light transmission in the range of about 200 nm to about 1100 nm.

That is, the mineral particles and the polymer matrix, independently, may have a light transmission of about 200 nm, 225 nm, 250 nm, 275 nm, 300 nm, 325 nm, 350 nm, 375 nm, 400 nm, 425 nm, 450 nm, 475 nm, 500 nm, 525 nm, 550 nm, 575 nm, 600 nm, 625 nm, 650 nm, 675 nm, 700 nm, 725 nm, 750 nm, 775 nm, 800 nm, 825 nm, 850 nm, 875 nm, 900 nm, 925 nm, 950 nm, 975 nm, 1000 nm, 1025 nm, 1050 nm, 1075 nm, and/or 1100 nm.

In some embodiments the mineral particles and the polymer matrix, independently, may have a light transmission in the range of about 200 nm to about 1100 nm.

That is, the mineral particles and the polymer matrix, independently, may have a light transmission of in the range of about 200-250 nm, 250-300 nm., 300-350 nm, 350-400 nm, 400-450 nm, 450-500 nm, 500-550 nm, 550-600 nm, 600-650 nm, 650-700 nm, 700-750 nm, 750-800 nm, 800-850 nm, 850-900 nm, 900-950 nm, 950-1000 nm, 1000-1050 nm, and/or 1050-1100 nm.

In some embodiments, the mineral particles and the polymer matrix, independently, may absorb light in the range of about 10 nm to about 15000 nm.

In some embodiments, the mineral particles and the polymer matrix, independently, may absorb light in the range of about 10 nm to about 200 nm. That is, the mineral particles and the polymer matrix, independently, may absorb light at about 10 nm, 20 nm, 30 nm, 40 nm, 50 nm, 60 nm, 70 nm, 80 nm, 90 nm, 100 nm, 110 nm, 120 nm, 130 nm, 140 nm, nm, 160 nm, 170 nm, 180 nm, and/or 200 nm.

In some embodiments, the mineral particles and the polymer matrix, independently, may absorb light in the range of about 10 nm to about 200 nm. That is, the mineral particles and the polymer matrix, independently, may absorb light in the range of about 10-20 nm, 20-40 nm, 40-60 nm, 60-80 nm, 80-100 nm, 100-120 nm, 120-140 nm, 140-160 nm, 160-nm, and/or 180-200 nm.

In some embodiments, the mineral particles and the polymer matrix, independently, may absorb light in the range of about 200 nm to about 500 nm. That is, the mineral particles and the polymer matrix, independently, may absorb light at about 200 nm, 225 nm, 250 nm, 275 nm, 300 nm, 325 nm, 350 nm, 375 nm, 400 nm, 425 nm, 450 nm, 475 nm, and/or 500 mm.

In some embodiments, the mineral particles and the polymer matrix, independently, may absorb light in the range of about 200 nm to about 500 nm. That is, the mineral particles and the polymer matrix, independently, may absorb light in the range of about 200-250 nm, 250-300 nm, 300-350 nm, 350-400 nm, 400-450 nm, and/or 450-500 nm.

In some embodiments, the mineral particles and the polymer matrix, independently, may absorb light in the range of about 500 nm to about 1100 nm. That is, the mineral particles and the polymer matrix, independently, may absorb light at about 500 nm, 525 nm, 550 nm, 575 nm, 600 nm, 625 nm, 650 nm, 675 nm, 700 nm, 725 nm, 750 nm, 775 nm, 800 nm, 825 nm, 850 nm, 875 nm, 900 nm, 925 nm, 950 nm, 975 nm, 1000 nm, 1025 nm, 1050 nm, 11075 nm, and/or 1100 nm.

In some embodiments, the mineral particles and the polymer matrix, independently, may absorb light in the range of about 500 nm to about 1100 nm. That is, the mineral particles and the polymer matrix, independently, may absorb light in the range of about 500-550 nm, 550-600 nm, 600-650 nm, 650-700 nm, 700-750 nm, 750-800 nm, 800-850 nm, 850-900 nm, 900-950 nm, 950-1000 nm, 1000-1050 nm, and/or 1050-1100 nm.

In some embodiments, the mineral particles and the polymer matrix, independently, may absorb light in the range of about 1100 nm to about 15000 nm. That is, the mineral particles and the polymer matrix, independently, may absorb light at about 1100 nm, 1200 nm, 11300 nm, 1400 nm, 1500 nm, 11600 nm, 1700 nm, 1800 nm, 11900 nm, 2000 nm, 2100 nm, 2200 nm, 2300 nm, 2400 nm, 2500 nm, 2600 nm, 2700 nm, 2800 nm, 2900 nm, nm, 3100 nm, 3200 nm, 3300 nm, 3400 nm, 3500 nm, 3600 nm, 3700 nm, 3800 nm, nm, 4000 nm, 4100 nm, 4200 nm, 4300 nm, 4400 nm, 4500 nm, 4600 nm, 4700 nm, 4800 nm, 4900 nm, 5000 nm, 5100 nm, 5200 nm, 5300 nm, 5400 nm, 5500 nm, 5600 nm, nm, 5800 nm, 5900 nm, 6000 nm, 6100 nm, 6200 nm, 6300 nm, 6400 nm, 6500 nm, 6600 nm, 6700 nm, 6800 nm, 6900 nm, 7000 nm, 7100 nm, 7200 nm, 7300 nm, 7400 nm, 7500 nm, 7600 nm, 7700 nm, 7800 nm, 7900 nm, 8000 nm, 8100 nm, 8200 nm, 8300 nm, 8400 nm, 8500 nm, 8600 nm, 8700 nm, 8800 nm, 8900 nm, 9000 nm, 9100 nm, 9200 nm, 9300 nm, 9400 nm, 9500 nm, 9600 nm; 9700 nm, 9800 nm, 9900 nm, 110000 nm, 10100 nm, 10200 nm, 10300 nm, 10400 nm, 10500 nm, 10600 nm, 10700 nm, 10800 nm, 10900 nm, 11000 nm, 11100 nm, 11200 nm, 111300 nm, 11400 nm, 11500 nm, 111600 nm, 11700 nm, 11800 nm, 11900 nm, 12000 nm, 12100 nm, 12200 nm, 12300 nm, 12400 nm, 12500 nm, 12600 nm, 12700 nm, 12800 nm, 12900 nm, 13000 nm, 13100 nm, 13200 nm, 13300 nm, 13400 nm, 13500 nm, 13600 nm, 13700 nm, 13800 nm, 13900 nm, 14000 nm, 14100 nm, 14200 nm, 14300 nm, 14400 nm, 14500 nm, 14600 nm, 14700 nm, 14800 nm, 14900 nm, and/or 15000 nm.

In some embodiments, the mineral particles and the polymer matrix, independently, may absorb light in the range of about 1100 nm to about 15000 nm. That is, the 'mineral particles in the mineral powder may absorb light in the range of about 1100-11200 nm, 1200-1400 nm, 1400-1600 nm, 1600-1800 nm, 1800-2000 nm, 2000-2200 nm, 2200-2400 mini, 2400-2600 nm, 2600-2800 nm, 2800-3000 nm, 3000-3200 nm, 3200-3400 nm, 3400-/1111, 3600-3800 nm., 3800-4000 nm, 4000-4200 nm, 4200-4400 nm, 4400-4600 nm, 4800 nm, 4800-5000 nm, 5000-5200 nm, 5200-5400 nm, 5400-5600 nm, 5600-5800 nm, 5800-6000 nm, 6000-6200 nm, 6200-6400 nm, 6400-6600 ma., 6600-6800 nm, 6800-7000 nm, 7000-7200 nm, 7200-7400 nm, 7400-7600 nm, 7600-7800 nm, 7800-8000 nm., 8200 nm, 8200-8400 nm, 8400-8600 nm, 8600-8800 nm, 8800-9000 nm, 9000-9200 nm, 9200-9400 nm, 9400-9600 nm, 9600-9800 nm, 9800-10000 nm, 10000-10200 nm, 10400 nm, 10400-10600 nm, 10600-10800 nm, 10800-11000 nm, 11000-11200 nm, 11400 nm, 11400-11600 nm, 11600-11800 nm, 11800-12000 nm, 12000-12200 nm, 12400 nm, 12400-12600 nm, 12600-12800 nm, 12800-13000 nm, 13000-13200 nm, 13400 nm, 13400-13600 nm, 13600-13800 nm, 13800-14000 nm, 14000-14200 nm, 14400 nm, 14400-14600 nm, 14600-14800 nm, and/or 14800-15000 nm. In some embodiments, the mineral particles and the polymer matrix, independently, may polarize light in the range of about 200 nm to about 15000 nm.

In some embodiments, the mineral particles and the polymer matrix, independently, may polarize light in the range of about 200 nm to about 500 nm, That is, the mineral particles and the polymer matrix, independently, may polarize tight at about 200 nm, 225 nm, 250 nm, 275 nm, 300 um, 325 nm, 350 nm., 375 nm, 400 nm, 425 nm, 450 nm, 475 nm, and/or 500 nm.

In some embodiments, the mineral particles and the polymer matrix, independently, may polarize light in the range of about 200 nm to about 500 nm, That is, the mineral particles and the polymer matrix, independently, may polarize light in the range of about 200-250 nm, 250-300 nm, 300-350 nm, 350-400 nm, 400-450 nm, and/or 450-500 nm.

In some embodiments, the mineral particles and the polymer matrix, independently, may polarize light in the range of about 500 nm to about 1100 nm. That is, the mineral particles and the polymer matrix, independently, may polarize light at about 500 nm, 525 nm, 550 nm, 575 nm, 600 nm, 625 nm, 650 nm, 675 nm, 700 nm, 725 nm, 750 nm, 775 nm, 800 nm, 825 nm, 850 nm, 875 nm, 900 nm, 925 nm, 950 nm, 975 nm, 1000 nm, 102.5 nm, nm, 1075 nm, and/or 1100 nm.

In some embodiments, the mineral particles and the polymer matrix, independently, may polarize light in the range of about 500 nm to about 1100 nm. That is, the mineral particles and the polymer matrix, independently, may polarize light in the range of about 500 nm, 525 nm, 550 nm, 575 nm, 600 nm, 625 nm, 650 nm, 675 nm, 700 nm, 725 nm, 750 nm, 775 nm, 800 nm, 825 nm, 850 nm, 875 nm, 900 nm, 925 nm, 950 nm, 975 nm, 1000 nm, 1025 nm, 1050 nm, 1075 nm, and/or 1100 nm.

In some embodiments, the mineral particles and the polymer matrix, independently, may polarize light in the range of about 1100 nm to about 15000 nm. That is, the mineral particles and the polymer matrix, independently, may polarize light at about 1100 nm, 1200 nm, 1300 nm, 1400 nm, 1500 nm, 1600 nm, 1700 nm, 1800 nm, 1900 nm, 2000 nm, nm, 2200 nm, 2300 nm, 2400 nm, 2500 nm, 2600 nm, 2700 nm, 2800 nm, 2900 nm, urn, 3100 nm, 3200 nm, 3300 nm, 3400 nm, 3500 nm, 3600 nm, 3700 nm, 3800 nm, 3900 nm, 4000 nm, 4100 nm, 4200 nm, 4300 nm, 4400 nm, 4500 nm, 4600 nm, 4700 nm, nm, 4900 nm, 5000 nm, 5100 nm, 5200 nm, 5300 nm, 5400 nm, 5500 nm, 5600 nm, 5700 nm, 5800 nm, 5900 nm, 6000 nm, 6100 nm, 6200 nm, 6300 nm, 6400 nm, 6500 nm, urn, 6700 nm, 6800 nm, 6900 nm, 7000 nm, 7100 nm, 7200 nm, 7300 nm, 7400 nm, 7500 nm, 7600 urn, 7700 nm, 7800 nm, 7900 nm, 8000 nm, 8100 nm, 8200 nm, 8300 nm, nm, 8500 nm, 8600 nm, 8700 nm, 8800 nm, 8900 nm, 9000 nm, 9100 nm, 9200 nm, 9300 nm, 9400 nm, 9500 nm, 9600 nm, 9700 nm, 9800 nm, 9900 nm, 10000 nm, 10100 nm, 10200 nm, 10300 nm, 10400 nm, 10500 nm, 10600 nm, 10700 nm, 10800 nm, 10900 nm, 11000 nm, 11100 nm, 11200 nm, 11300 nm, 11400 nm, 11500 nm, 11600 nm, 11700 nm, 11800 nm, 11900 nm, 12000 nm, 12100 nm, 12200 nm, 12300 nm, 12400 nm, 12500 nm, 12600 nm, 12700 nm, 12800 nm, 12900 nm, 13000 nm, 13100 nm, 13200 nm, 13300 urn, 13400 nm, 13500 nm, 13600 nm, 13700 nm, 13800 nm, 13900 nm, 14000 nm, 14100 nm, 14200 nm, 14300 nm, 14400 nm, 14500 nm, 14600 nm, 14700 nm, 14800 nm, 14900 nm, and or 15000 nm.

In some embodiments, the 'mineral particles and the polymer matrix, independently, may polarize light in the range of about 1100 nm to about 15000 nm, That is, the mineral particles and the polymer matrix, independently, may polarize light in the range of about 1100-1200 nm, 1200-1400 nm, 1400-1600 nm, 1600-1800 nm, 1800-2000 nm, 2000 nm, 2200-2400 nm, 2400-2600 nm, 2600-2800 nm, 2800-3000 nm, 3000-3200 nm, 3400 nm, 3400-3600 nm, 3600-3800 nm, 3800-4000 nm, 4000-4200 nm, 4200-4400 nm, 4400-4600 nm, 4600-4800 nm, 4800-5000 nm, 5000-5200 nm, 5200-5400 nm, 5400 nm, 5600-5800 nm, 5800-6000 nm, 6000-6200 nm, 6200-6400 nm, 6400-6600 nm, 6600-6800 nm, 6800-7000 nm, 7000-7200 nm, 7200-7400 nm, 7400-7600 nm, 7600-7800 nm, 7800-8000 nm, 8000-8200 nm, 8200-8400 ran, 8400-8600 nm, 8600-8800 nm, 8800-nm, 9000-9200 nm, 9200-9400 nm, 9400-9600 nm, 9600-9800 nm, 980010000 nm, 10200 nm, 10200-10400 nm, 10400-10600 nm, 10600-10800 nm, 10800-11000 nm, 11200 nm, 11200-11400 nm, 11400-11600 nm, 11600-11800 nm, 11800-12000 nm, 12200 nm, 12200-12400 nm, 12400-12600 nm, 12600-12800 nm, 12800-13000 nm, 13200 nm, 13200-13400 nm, 13400-13600 nm, 13600-13800 nm, 13800-14000 nm, 14200 nm, 14200-14400 nm, 14400-14600 nm, 14600-14800 nm, and/or 14800-15000 nm.

In some embodiments, the mineral particles and the polymer matrix, independently, may polarize light completely. In other embodiments, the mineral particles and the polymer matrix, independently, may polarize light partially.

In some embodiments, the mineral particles and the polymer matrix, independently, may emit light in the range of about 200 um to about 1100 nm. That is, the mineral particles in the mineral powder may emit light at about 200 nm, 225 nm, 250 nm, 275 nm, 300 nm, 325 nm, 350 nm, 375 nm, 400 nm, 425 nm, 450 nm, 475 nm, 500 nm, 525 nm, 550 nm, 575 nm, 600 nm, 625 nm, 650 nm, 675 nm, 700 nm, 725 nm, 750 nm, 775 nm, 800 nm, 825 nm, 850 nm, 875 nm, 900 nm, 925 nm, 950 nm, 975 nm, 1000 nm, 1025 nm, 1050 nm, 1075 nm, and/or 1100 nm.

In some embodiments, the mineral particles and the polymer matrix, independently, may emit light in the range of about 200 nm to about 1100 nm. That is, the mineral particles and the polymer matrix, independently, may emit light in the range of about 200-250 nm, 250-300 nm, 300-350 nm, 350-400 nm, 400-450 um, 450-500 nm, 500-550 nm, 550-600 nm, 600-650 nm, 650-700 nm, 700-750 nm, 750-800 nm, 800-850 nm, 850-900 nm, 900-950 nm, 950-1000 nm, 10001050 nm, and/or 1050-1100 nm.

Active Polymer Material Manufacturing

Once the polymer matrix is chosen and the mineral is selected and ground into a powder of desired size and shape, the active polymer material is constructed.

In some embodiments, the mineral powder may be dispersed, suspended, embedded, or otherwise incorporated into the polymer matrix by methods known in the art, such as in a rotating drum with paddle-type mixers. In other embodiments, the mineral powder may be introduced to the polymer matrix by other processes known in the art such as compounding. The examples of the process of grinding and combining can be found in U.S. Pat. Nos. 6,204,317, 6,214,264, and 6,218,007.

In some embodiments, the polymer matrix may initially be in pellet form and dried to remove moisture by using, for example, a desiccant dryer. In some embodiments, heating or cooling may be necessary prior and/or during the steps of dispersing, suspending, embedding, or incorporating the mineral to obtain an even dispersion.

In some embodiments, once the mineral is dispersed in the polymer matrix, the resulting active polymer material may be cured or hardened.

In sonic embodiments, the mineral comprise about 0.5% to about 20% of the active polymer material. That is, the mineral may comprise about 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5% or 20% of the active polymer material.

In some embodiments, the mineral comprise from about 0.5% to about 20% of the active polymer material. That is, the mineral may comprise in the range of about 0.5-1.0%, 1.0-1.5%, 1.5-2.0%, 2.0-2.5%, 2.5-3.0%, 3.0-4.0%, 4.0-5.0%, 5.0-6.0%, 6.0-7.0%, 7.0-8.0%, 8.0-9.0%, 9.0-10.0%, 10.0-11.0%, 11.0-12.0%, 12.0-13.0%, 13.0-14.0%, 14.0-15.0%, 15.0-16.0%, 16.0-17.0%, 17.0-18.0%, 18.0-19.0%, or 19.0-20% of the active polymer material.

In some embodiments, the active polymer material is Celliant (U.S. Pat. No. 7,074,499).

Manipulation of Active Polymer Material

The APM described herein can be manipulated into different forms depending on the application requirements. In some embodiments, the APM can be formed into useful building blocks such as fibers or films. In other embodiments, the APM is formed into small beads or particles having an average size of less than about 5 cm, less than about 1 cm, or less than about 0.5 cm.

Once the mineral powder and the polymer matrix are combined, the resulting liquid, viscous oil, or semi-solid may be extruded into various shapes and forms. In some embodiments, the APM is extruded into a fiber. In other embodiments, the APM is extruded into staple fibers of various lengths. The examples of this process of extrusion, known in the art, can be found in previously disclosed references and in U.S. Pat. No. 6,067,785.

In some embodiments, once the active polymer material is extruded into various forms, it may need to be dried, cured, and/or hardened.

Once the polymer material system is extruded into a fiber form, in some embodiments, the fibers may be combined together by a spinning process, for example using a rotary spinning machine, to yield a yarn. The range of the size of the apertures in the rotary spinning machine may be from about 6 microns to about 30 microns.

In some embodiments, the step of spinning the fibers into a yarn comprises spinning staple fiber having a denier per fiber of between about 1 and about 3; accordingly, the prior step of spinning the melted polyester into fiber likewise comprises forming a fiber of those dimensions. The fiber is typically heat set before being cut into staple fibers with conventional techniques. While the extruded fibers are solidifying, they may be drawn by methods known in the art to impart strength.

In some embodiments, yarn made of the APM is further formed into fabrics or textiles, typically woven or knitted fabrics by combination with both natural and synthetic fibers. Non-limiting examples of natural fibers may include cotton, wool, hemp, silk, ramie, and jute. Non-limiting examples of synthetic fibers may include acrylic, acetate, Lycra, spandex, polyester, nylon, and rayon.

In some embodiments, yarn made of the APM is dyed. In other embodiments, the fabric or textile made of the APM comprising yarn may be dyed. Dyes can be synthetic or natural. Non-limiting examples of the types of dyes include direct, acid, disperse, reactive, basic, mordant, sulfur and vat dyes.

In some embodiments, yarn made of the APM is incorporated into blends with cotton and polyester in any proportion. In some embodiments, the blend includes between about 35% and about 65% by weight of cotton with the remainder being polyester. That is, said blend may be about 35/65 (35% by weight of cotton and 65% by weight of polyester), 36/64, 37/63, 38/62, 39/61, 40/60, 41/59, 42/58, 43/57, 44/56, 45/55, 46/54, 47/53, 48/52, 49/51, 50/50, 51/49, 52/48, 53/47, 54/46, 55/45, 56/44, 57/43, 58/42, 59/41, 60/40, 61/39, 62/38, 63/37, 64/36, or 65/35.

In some embodiments, yarn made of the APM is incorporated into blends with cotton and polyester of 50% cotton and 50% polyester (50/50).

In some embodiments, the APM can be produced into different fibers.

Other methods of production of fibers are equally suitable such as those described in U.S. Pat. Nos. 3,341,512; 3,377,129; 4,666,454; 4,975,233; 5,008,230; 5,091,504; 5,135,697; 5,272,246; 4,270,913; 4,384,450; 4,466,237; 4,113,794; and 5,694,754, all of which are expressly incorporated by reference in their entirety herein.

In some embodiments, the APM is extruded into a staple fiber with a length in the range of about 0.1 cm to 15 cm. That is, the staple fiber may be about 0.1 cm, 0.2 cm, 0.3 cm, 0.4 cm, 0.5 cm, 0.6 cm, 0.7 cm, 0.8 cm, 0.9 cm, 1.0 cm, 1.1 cm, 1.2 cm, 1.3 cm, 1.4 cm, 1.5 cm, 1.6 cm, 1.7 cm, 1.8 cm, 1.9 cm, 2.0 cm, 2.1 cm, 2.2 cm, 2.3 cm, 2.4 cm, 2.5 cm, 2.6 cm, 2.7 cm, 2.8 cm, 2.9 cm, 3.0 cm, 3.1 cm, 3.2 cm, 3.3 cm, 3.4 cm., 3.5 cm, 3.6 cm, 3.7 cm., 3.8 cm., 3.9 cm, 4.0 cm, 4.1 cm, 4.2 cm, 4.3 cm, 4.4 cm, 4.5 cm, 4.6 cm, 4.7 cm, 4.8 cm, 4.9 cm, 5.0 cm, 5.1 cm, 5.2 cm, 5.3 cm, 5.4 cm, 5.5 cm, 5.6 cm, 5.7 cm, 5.8 cm, 5.9 cm, 6.0 cm, 6.1 cm, 6.2 cm, 6.3 cm, 6.4 cm, 6.5 cm, 6.6 cm., 6.7 cm, 6.8 cm, 6.9 cm, 7.0 cm, 7.1 cm, 7.2 cm, 7.3 cm, 7.4 cm, 7.5 cm, 7.6 cm, 7.7 cm, 7.8 cm, 7.9 cm, 8.0 cm, 8.1 cm, 8.2 cm, 8.3 cm, 8.4 cm, 8.5 cm, 8.6 cm, 8.7 cm, 8.8 cm, 8.9 cm, 9.0 cm, 9.1 cm, 9.2 cm, 9.3 cm, 9.4 cm, 9.5 cm, 9.6 cm, 9.7 cm, 9.8 cm, 9.9 cm, 10.0 cm, 10.1 cm, 10.2 cm, 10.3 cm, 10.4 cm, 10.5 cm, 10.6 cm, 10.7 cm., 10.8 cm, 10.9 cm, 11.0 cm, 11.1 cm, 11.2 cm, 11.3 cm, 11.4 cm, 11.5 cm, 11.6 cm, 11.7 cm, 111.8 cm, 11.9 cm, 12.0 cm, 112.1 cm, 12.2 cm, 12.3 cm, 12.4 cm, 12.5 cm, 12.6 cm, 12.7 cm, 12.8 cm, 1.2.9 cm, 13.0 cm, 13.1 cm, 13.2 cm, 13.3 cm, 13.4 cm, 13.5 cm., 13.6 cm, 13.7 cm, 13.8 cm, 13.9 cm, 14.0 cm, 14.1 cm, 14.2 cm, 14.3 cm, 14.4 cm, 14.5 cm, 14.6 cm, 14.7 cm, 14.8 cm, 14.9 cm, or 15.0 cm.

In some embodiments, the polyester mixture may be used to create a staple fiber. The staple fiber may then be used to create a non-woven membrane. 'This membrane may be bonded to another fabric, membrane, or material. In some embodiments, staple fibers made from APM can be non-woven into a batting material.

In some embodiments, the APM is extruded into a film with a thickness in the range of about 0.05 mm to 1.00 mm. That is, the film extruded from the APM may have a thickness of about 0.05 mm, 0.06 mm, 0.07 mm, 0.08 mm, 0.09 mm, 0.10 mm, 0.11 mm, 0.12 mm, 0.13 mm, 0.14 mm, 0.15 mm, 0.16 mm, 0.17 mm, 0.18 mm, 0.19 mm, 0.20 mm, 0.21 mm, 0.22 mm, 0.23 nm, 0.24 mm, 0.25 mm, 0.26 mm, 0.27 mm, 0.28 mm, 0.29 mm, 0.30 mm, 0.31 mm, 0.32 mm, 0.33 mm, 0.34 mm, 0.35 mm, 0.36 mm, 0.37 mm, 0.38 mm, 0.39 mm, 0.40 mm, 0.41 mm, 0.42 mm, 0.43 mm, 0.44 mm, 0.45 mm, 0.46 mm, 0.47 mm, 0.48 mm, 0.49 mm, 0.50 mm, 0.51 mm, 0.52 mm, 0.53 mm, 0.54 mm, 0.55 mm, 0.56 mm, 0.57 mm, 0.58 mm, 0.59 mm, 0.60 mm, 0.61 mm, 0.62 mm, 0.63 mm, 0.64 mm, 0.65 mm, 0.66 mm, 0.67 mm, 0.68 mm, 0.69 mm, 0.70 mm, 0.71 mm, 0.72 mm, 0.73 mm, 0.74 mm, 0.75 mm, 0.76 mm, 0.77 mm, 0.78 mm, 0.79 mm, 0.80 mm, 0.81 mm, 0.82 mm, 0.83 mm, 0.84 mm, 0.85 mm, 0.86 mm, 0.87 mm, 0.88 mm, 0.89 mm, 0.90 mm, 0.91 mm, 0.92 mm, 0.93 mm, 0.94 mm, 0.95 mm, 0.96 mm, 0.97 mm, 0.98 mm, 0.99 mm, or 1.00 mm.

In some embodiments, the ARM is extruded into a film with a thickness in the range of about 0.05 mm to 0.5 mm. That is, the film extruded from the active polymer material may have a thickness in the range of about 0.05-0.06 mm, 0.06-0.08 mm, 0.09-0.10 mm, 0.10-0.12 mm, 0.12-0.14 mm, 0.14-0.16 mm, 0.16-0.18 mm, 0.18-0.20 mm, 0.20-0.22 mm, 0.22-0.24 mm, 0.2.4-0.26 mm, 0.26-0.28 mm, 0.28-0.30 mm, 0.30-0.32 mm, 0.32-0.3.4 mm, 0.34-0.36 mm, 0.36-0.38 mm, 0.38-0.40 nm, 0.40-0.42 mm, 0.42-0.44 mm, 0.44-0.46 mm, 0.46-0.48 mm, or 0.48-0.50 mm, In some embodiments, the APM is extruded, woven, or non-woven into a sheet with a thickness in the range of about 1 mm to 100 ram. That is, the film extruded from the APNI may have a thickness of about 1 mm, 2 mm, 3 mm, 4 mm, 5 mm, 6 mm, 7 mm, 8 mm, 9 mm, mm, 11 mm, 12 mm, 13 mm, 14 mm, 15 mm, 16 mm, 17 mm, 18 mm, 19 mm., 20 mm, mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 51 mm, 52 mm, 53 mm, 54 mm, 55 mm, 56 mm, 57 mm, 58 mm, 59 mm, 60 mm, 61 mm, 62 mm, 63 mm, 64 mm, 65 mm, 66 mm, 67 mm, 68 mm, 69 mm, 70 mm, 71 mm, 72 mm, 73 nm, 74 mm, 75 mm, 76 mm, 77 mm, 78 mm, 79 mm, 80 mm, 81 mm, 82 mm, 83 mm, 84 mm, 85 mm, 86 mm, 87 mm, 88 mm, 89 mm, 90 mm, 91 mm, 92 mm, 93 mm, 94 mm, 95 mm, 96 mm, 97 mm, 98 mm, 99 mm, or 100 mm.

Products Made from Active Polymer Material Useful in Agriculture

As described herein, the APM can be extruded into different types of fibers to form fabrics or textiles or it can be extruded into a film. These materials can then be transformed into various products that are useful in agricultural settings. In some embodiments, the APM is a solid. In another embodiment, the APM is a semi-solid. For examples of non-*cannabis* plant/agricultural applications, see U.S. Patent Application Publication No. 2016/0081281 and International Publication No. WO 2016/049025 (Active Polymer Material for Agricultural Use), each of which is specifically incorporated by reference herein in its entirety.

In some embodiments, a fabric comprising the APM can be formed into a bag used to hold *cannabis* plants. The bag may, in some embodiments, hold the growth media and the *cannabis* plant. In some embodiments, the bag is meshed.

Standard *cannabis* plant bags, such as burlap or polypropylene bags, do not have the material that is capable of storing and emitting photons that may, in some embodiments, assist in *cannabis* plant growth.

In other embodiments, a fabric, a film, a sheet, a batting material, or a composition of staple fibers comprising the .APM may be used to wrap the roots or roots and growth media surrounding the roots of a *cannabis* plant. In some embodiments, said fabric, film, or sheet may be meshed.

In some embodiments the APMs of the present invention are used to produce soil covers. In some embodiments, a fabric, a film, a sheet, a batting material, and a composition of staple fibers comprising the APM may be placed on top of the soil. In other embodiments, said fabric, film, sheet, batting material or a composition of staple fibers may be placed on top of the soil and around the stem of the *cannabis* plant. In some embodiments, said fabric, film, or sheet may be meshed. In other embodiments, said fabric, film, or sheet may be cut to create an opening to accommodate the stem of the *cannabis* plant. In some embodiments, said fabric, film, or sheet may be meshed.

In some embodiments, the soil covers of the present invention warm. The soil by trapping heat and/or transmitting IR radiation, mitigate weed growth by blocking visible light, and reflect light towards the *cannabis* plants for additional energy and warding off pests. In some embodiments the soil cover of the present invention is infused with pesticides, or other chemicals for additional protection of the *cannabis* plants (see for example U.S. Pat. Nos. 3,590,528; 7,247,311; 5,879,695; 5,532,298; and 8,142,804).

In some embodiments, the soil covers of the present invention are colored to further tailor the light absorption, transmission, and reflection beneficial for *cannabis* plant protection or growth (see for example U.S. Pat. Nos. 5,138, 792 and 6,601,338).

In some embodiments, a fabric, a film, a sheet, a batting material, and a composition of staple fibers comprising the APM may be mixed into the growth media of the *cannabis* plant. In some embodiments, said fabric, film, or sheet may be cut into smaller pieces prior to mixing with the growth media. In some embodiments, said fabric, film, or sheet may be meshed.

In some embodiments, a fabric, a film, a sheet, a batting material, or a composition of staple fibers comprising the APM may be mixed with mulch. In some embodiments, said fabric, film, or sheet may be cut into smaller pieces prior to mixing with mulch. In some embodiments, said fabric, film, or sheet may be meshed.

In some embodiments, a fabric, a film, a sheet, a batting material, or a composition of staple fibers comprising the APM may be used as mulch.

In some embodiments, said fabric, film, or sheet may be cut into smaller pieces prior to use for said mulch. In. some embodiments, said fabric, film, or sheet may be meshed.

Mulch act similarly to soil covers by retaining soil warmth and blocking sunlight to pass to the soil. In some embodiments, the APM mulch of the present invention may exhibit water and nutrient retaining properties (see for example U.S. Pat. Nos. 5,649,495; 5,868,087; and 7,459, 501). In some embodiments, the water-retaining APM mulch of the present invention may be especially useful in dry climates. In some embodiments, the APM mulch of the present invention is processed into small particles such that it does not affect the soil composition as it swells when water is absorbed.

In some embodiments, a fabric, a film, or a sheet comprising the APM may be placed over the *cannabis* plant as a cover. In some embodiments, the cover may enclose the *cannabis* plant completely.

In other embodiments, the cover may only provide partial coverage of the *cannabis* plant. In some embodiments, the cover may come in contact with the *cannabis* plant. In other embodiments, the cover may not be in contact with the *cannabis* plant. In some embodiments, said fabric, film, or sheet may be meshed.

In some embodiments, the APM of the present invention may be used to produce *cannabis* plant protectors. In some embodiments, a fabric, a film, or a sheet comprising the APM may be placed around the *cannabis* plant forming a cylindrical shape. In some embodiments, said fabric, film, or sheet may be placed around the *cannabis* plant forming an arch (i.e. not completely enclosed in a cylindrical shape). In some embodiments, said fabric, film, or sheet may be meshed. In some embodiments, said *cannabis* plant protector may be inflatable.

In some embodiments, a fabric, a batting material, or a composition of staple fibers comprising the APM may be used as the growth media for the *cannabis* plant. In other embodiments, said fabric, batting material, or composition of staple fibers may be used as a component in the growth media mixture.

In some embodiments, the APM may be chemically incorporated or embedded into *cannabis* planting pots and *cannabis* planting containers.

Non-Limiting Uses for Active Polymer Material

The APM that has been formed in various shapes as described previously can, in some embodiments, be placed in close proximity to a *cannabis* plant, a *cannabis* plant part, or a *cannabis* plant tissue culture. In some embodiments, said APM can be mixed in with the growth media of the *cannabis* plant.

In other embodiments, said APM is the growth media of the *cannabis* plant.

In some embodiments, at least one part of the said APM is placed within 100 cm. of the *cannabis* plant, *cannabis* plant part, or *cannabis* plant tissue culture. That is, at least one part of the said APM is placed at about 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm., 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm., 41 cm., 42 cm., 43 cm., 44 cm, 45 cm, 46 cm, 47 cm, 48 cm, 49 cm, 50 cm, 51 cm, 52 cm, 53 cm, 54 cm, 55 cm, 56 cm, 57 cm, 58 cm, 59 cm, 60 cm, 61 cm, 62 cm, 63 cm, 64 cm, 65 cm, 66 cm, 67 cm, 68 cm, 69 cm, 70 cm, 71 cm, 72 cm, 73 cm., 74 cm, 75 cm., 76 cm, 77 cm, 78 cm, 79 cm, 80 cm, 81 cm, 82 cm, 83 cm, 84 cm, 85 cm, 86 cm, 87 cm, 88 cm, 89 cm, 90 cm, 91 cm, 92 cm, 93 cm, 94 cm, 95 cm, 96 cm, 97 cm, 98 cm, 99 cm, or 100 cm from a *cannabis* plant, a *cannabis* plant part, or a *cannabis* plant tissue culture.

In some embodiments, at least one part of the said APM touches the *cannabis* plant, *cannabis* plant part, or tissue culture.

In some embodiments, the APM can be reused. In other embodiments, the APM can be reused multiple times.

Once the APM is placed in close proximity to and/or touching the *cannabis* plant, normal care should ensure proper growth of the *cannabis* plant.

Active Polymer Material Kits

In some embodiments, the APM described previously can form a kit with another material that would benefit to be used in combination. Said kit may comprise the APM and a *cannabis* plant, a *cannabis* plant part, or a *cannabis* plant tissue culture. In some embodiments, said kit is a bagged or a potted *cannabis* plant. In some embodiments, said kit comprises seeds, bulbs, tubers, tuberous roots, rhizomes, and/or corms which are embedded or enclosed in said active polymer material.

In some embodiments, a kit may comprise the APM and a *cannabis* planting pot or a *cannabis* planting container. In some embodiments, said kit comprises the APM to be placed inside the *cannabis* planting pot or the *cannabis* planting container. In other embodiments, said kit comprises a *cannabis* planting pot or the *cannabis* planting container where the wall of said pot or container is lined with the APM.

In some embodiments, a kit may comprise the APM and *cannabis* plant growth media. Said kit may comprise *cannabis* plant growth media that is mixed in with APM. In other embodiments, said kit comprises the APM layered on or placed in between the *cannabis* plant growth media. In some embodiments, the kit may comprise the APM integrated into *cannabis* plant growth media in which a *cannabis* plant or a *cannabis* plant part, such as a *cannabis* plant seed, is placed or embedded.

EXAMPLES

Example 1: Formation of Active Polymer Material

The mineral particles of titanium dioxide, silicon carbide, and aluminum oxide are ground to a fine powder in a composition of 30:60:10 (i.e., 3:6:1), respectively. The mineral powder composition (100 pounds) was mixed with PET resin (1000 pounds) in a heated rotating drum with paddle-type mixers. This produced active polymer material comprising about 1 percent of mineral by weight of the total weight of the active polymer material.

Example 2: Extruding Active Polymer Material into a Fiber

An active polymer material which was produced as described in Example 1, which is a viscous liquid, was passed through a spinneret to form, continuous filaments of semi-solid material, which is then solidified upon cooling.

Example 3: Extruding Active Polymer Material into a Staple Fiber

An active polymer material fiber which was produced as described in Example 2 was cut in shorter uniform strands of about 3 cm to obtain staple fibers.

Example 4: Formation of Non-woven Batting Material

A staple fiber made with an active polymer material, produced as described in Example 3, was combined together in a non-woven fashion to form a batting material.

Example 5: Formation of Non-woven Batting Material in Spherical Shapes

A staple fiber made with an active polymer material, produced as described in Example 3, was combined together in a non-woven fashion and rolled to a spherical shape having a diameter of about 2 cm.

Example 6: Extruding Active Polymer Material into a Film

An active polymer material which was produced as described in Example 1, which is a viscous liquid, was passed through a plastic extruder to form a uniform and continuous thin film having thickness of about 0.5 mm.

Example 7: Comparison Study of Active Polymer Material

An active polymer material, comprising of Celliant™, was extruded into undyed polyester fibers pry 75/36) and knitted to form a fabric (100% APM). A controlled fabric was prepared by knitting undyed polyester fibers (DTY 75/36) which contained no APM (Control). The reflectance, transmittance, and absorbance properties of these fabrics were studied. The obtained data are shown in Table 1. The measurements were made in accordance with ASTM (American Society for Testing and Materials) standard test method E903, Solar Absorbance, Reflectance, and Transmittance of Material Using Integrating Spheres. The uncertainty in the measurement statistic is ±0.03 of a full-scale value of 1.0. The repeatability of the measurement statistic is ±0.005 of a full-scale value of 1.0. The instrument used was LPSR 200 IR (S/N 108) by AZ Technology, Inc., with sphere geometry of absolute integrating sphere of 15°/h. The solar spectral irradiance distribution and the weighting method used for the computation of the solar optical property are in compliance with the standard as called out in paragraphs of section 8.3 of ASTM E903.

Table 1 illustrates that the fabric made with active polymer material system absorbs solar radiation in greater amount than the control fabric which contained no mineral compounds.

TABLE 1

Optical Properties: Full scale = 1.000

| Sample | Solar Reflectance* | Solar Transmittance* | Solar Absorbance* |
|---|---|---|---|
| 100% APM | 0.512 | 0.190 | 0.298 |
| Control | 0.610 | 0.214 | 0.176 |

*At air mass = 0.

Example 8: Comparison Study of Active Polymer Material

An active polymer material, comprising of Celliant™, was extruded into fibers, undyed, and knitted to form a fabric (100% APM, F1). The same active polymer material that was extruded into fibers and dyed in black was knitted with black polyester fibers in a 1:1 ratio (50% APM, F2). A controlled fabric was prepared by knitting black polyester fibers which contained no active polymer material (Control, F3). The reflectance, transmittance, and absorbance properties of the three fabrics were studied using the real solar spectrum, namely the incidental solar spectrum on the ground considering the atmospheric absorption.

The obtained data are shown in Tables 2-4. The measurements were obtained using spectrometers (Perkin Elmer and Bio-rad) at an ambient temperature.

The results in Tables 2-4 demonstrate that the largest optical property differences between the fabrics are in the interaction with the close IR spectrum. In particular, active polymer material (F1) demonstrates improved absorption of the close IR at 17.74% when compared to the control material (F3) of 5.79%.

TABLE 2

Reflectance Study Results: % of the source which is reflected on the fabric

| Sample | Total Reflectance | Reflectance [0.3-0.4 μm][1] UV Range | Reflectance [0.4-0.78 μm][2] Visible Range | Reflectance [0.78-2.2 μm][3] Close IR Range |
|---|---|---|---|---|
| 100% APM (F1) | 20.41 | 3.98 | 5.56 | 53.08 |
| 50% APM (F2) | 21.81 | 3.92 | 5.77 | 57.08 |
| Control (F3) | 22.02 | 3.94 | 5.80 | 57.69 |

[1] 300 nm-400 nm.
[2] 400 nm-780 nm.
[3] 780 nm-2200 nm.

TABLE 3

Transmittance Study Results: % of the source which transmits through the fabric

| Sample | Total Reflectance | Reflectance [0.3-0.4 μm][1] UV Range | Reflectance [0.4-0.78 μm][2] Visible Range | Reflectance [0.78-2.2 μm][3] Close IR Range |
|---|---|---|---|---|
| 100% APM (F1) | 11.97 | 3.32 | 4.11 | 29.19 |
| 50% APM (F2) | 13.20 | 3.50 | 4.36 | 32.57 |
| Control (F3) | 15.53 | 5.09 | 5.94 | 36.52 |

[1] 300 nm-400 nm.
[2] 400 nm-780 nm.
[3] 780 nm-2200 nm.

TABLE 4

Absorbance Study Results: % of the source which is absorbed by the fabric

| Sample | Total Reflectance | Reflectance [0.3-0.4 μm][1] UV Range | Reflectance [0.4-0.78 μm][2] Visible Range | Reflectance [0.78-2.2 μm][3] Close IR Range |
|---|---|---|---|---|
| 100% APM (F1) | 67.92 | 92.70 | 90.34 | 17.74 |
| 50% APM (F2) | 64.99 | 92.58 | 89.87 | 10.36 |
| Control (F3) | 62.44 | 90.97 | 88.25 | 5.79 |

[1] 300 nm-400 nm.
[2] 400 nm-780 nm.
[3] 780 nm-2200 nm.

These results demonstrate the effect of the active polymer materials of the present invention in altering specific light absorption, reflection, and transmittance properties. The Celliant active mineral composition of 55% SiC, 25% $TiO_2$, 5% $SiO_2$, and 15% increases the absorption of IR range wavelengths. In some embodiment, this formulation of Celliant demonstrates absorption and excitation of the solar radiation where 65% of the absorption is of the band in the infrared spectrum.

Example 9: Emittance Study of Active Polymer Material

An active polymer material, comprising of Celliant®, can be extruded into undyed polyester fibers (DTY 75/36) and knitted to form a fabric (100% .APM). A controlled fabric can be prepared by knitting undyed polyester fibers (DTY 75/36) which contained no APM (Control). The emittance properties of these fabrics are then studied. The measurements will be made in accordance with AZ Technology test methods for near-normal emittance and total hemispherical emittance at 300 K. Near-normal emittance measurements are traceable to ASTM standard test method E408 through round robin testing with the Gier Dunkel DB-100.

The instrument used will be TESA 2000 by AZ Technology, Inc., with absolute ellipsoidal cavity of 15/h. Prior to each use, the instrument will be calibrated using Hemispheric Emittance Calibration Puck by AZ Technology, Inc.

Example 10: Formation of an EcoBag with a *Cannabis* Plant

An active polymer material fiber which was produced as described in Example 2 can be woven into a potting bag with an opening of about 10 cm diameter and a depth of about 15 cm. The bags of this example can be used as temporary or permanent growth containers for *cannabis* tissue, plant parts and whole plants.

Example 11: Formation of a Collar (Soil Cover)

An active polymer batting material which was produced as described in Example 4 was die-cut in a square shape having a dimension of 10×10 cm with a circular opening in the center of about 2 cm diameter. The die-cut material was then placed around the stem of the *cannabis* plant.

Example 12: Formation of a Mulch Made with the Active Polymer Material

An active polymer material staple fiber, having length of about 1 cm, produced as described in Example 3 was non-woven into a spherical shape of approximately 1 cm in diameter. The resulting non-woven spherical shaped materials can be mixed in with the top layer of the soil surrounding a *cannabis* plant.

Example 13: Formation of a Soil Cover

An active polymer material film which was produced as described in Example 6 can be placed over a row of growth media. The film contained various opening to allow water permeation as well as to allow *cannabis* plant to grow.

Example 14: Comparison Study of *Cannabis* Plant Growth

Figure 3:
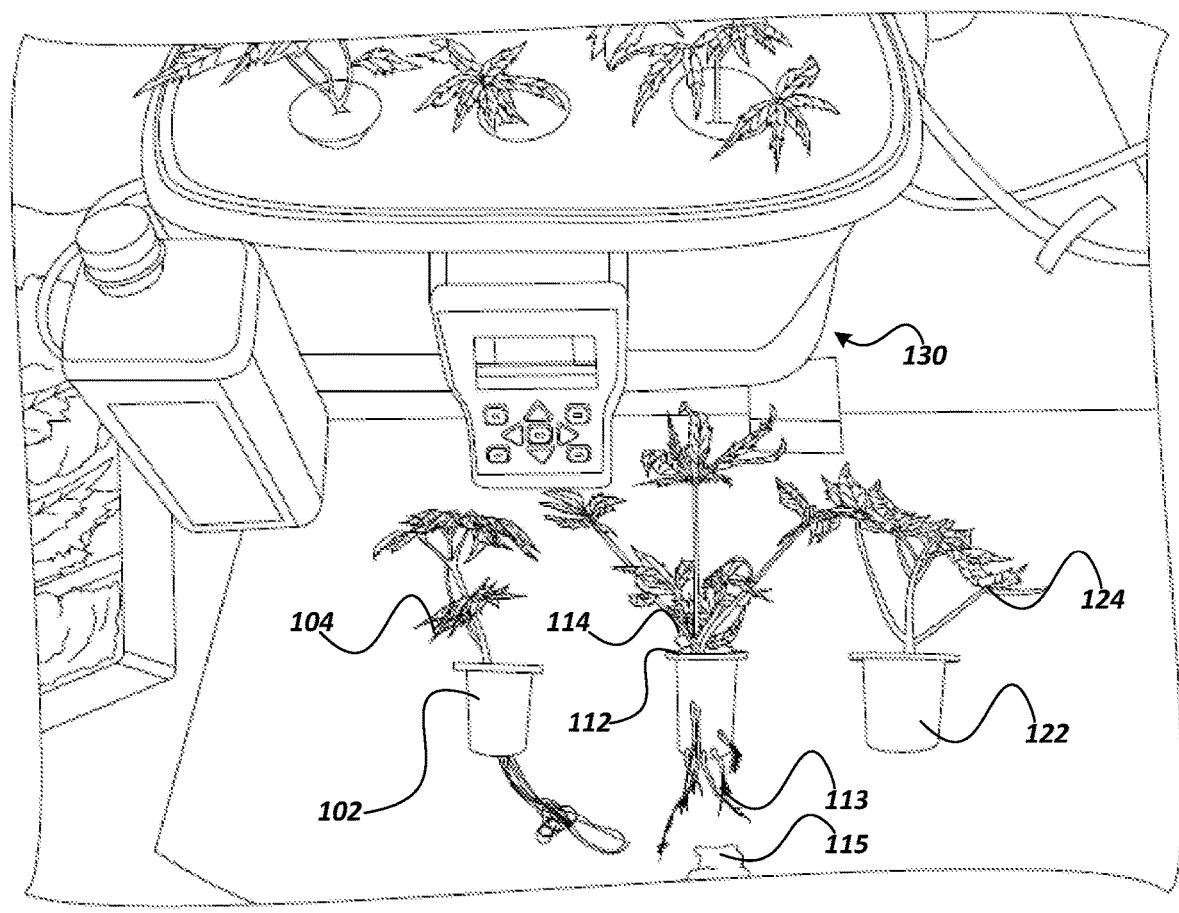
FIG. 3 is similar to FIG. 1 except it also includes a view of the physical system 130 used for growing the control 104, 124 and experimental 114 *cannabis* kits/plants.

Two separate types of *cannabis* plant containers 102, 112, 122 were prepared and tested according to the following procedure. Clones of *cannabis* plant strain 'Blueberry Kush' used for testing were each cut 4 inches high from same plant. For each set of three, two of the clones 104, 124 were placed in traditional rock wool which is the standard of the industry and placed in a conventional hydro grow device 130 (AeroGarden®) (FIG. 3).

Figure 2:
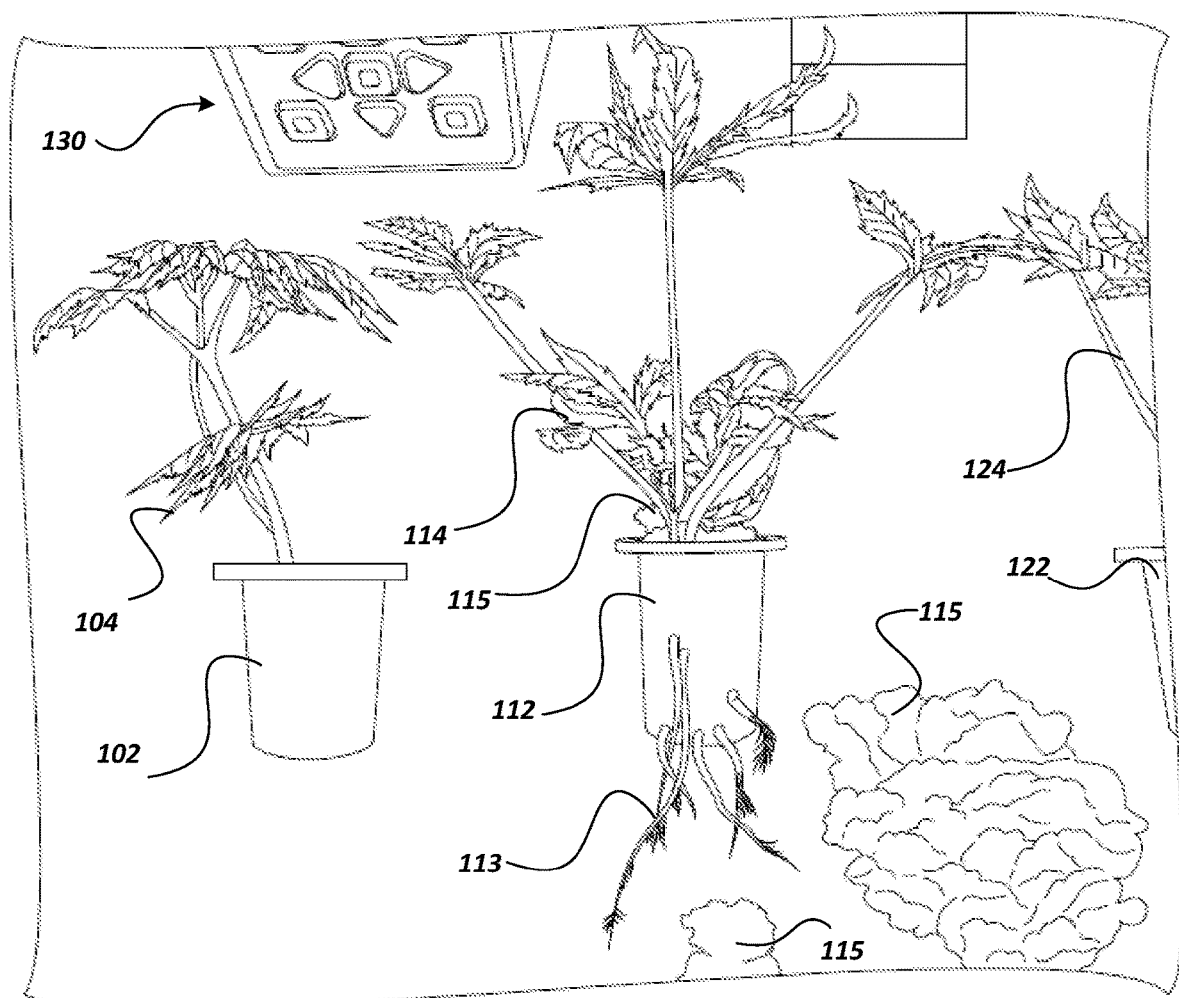
FIG. 2 is similar to FIG. 1 except it also includes a separate sample of the growing media 115 (see, lower right-hand corner) used to grow the experimental (i.e., center) plant 114.

The third clone 114 is placed in a net bag 112 comprising 2 grams of solar mulch 115 (FIG. 2) which is a polymer composite prepared according to the process set forth in Example 2. The netting helps retain a shape useful for holding and growing the plants. The solar mulch 115 is comprised of polyester staple fiber with a size of 1.8 denier by 1.5 inches. This staple fiber is then processed into small balls or spheres each being approximately the size of Q-tips®. The balls help to create an interlocking phenomenon that keeps the clone 114 upright. The *cannabis* clone 114 is placed in the center and then put into the same conventional hydro grow (AeroGarden®) device 130 (FIG. 3).

The hydro grow device 130 was set for a temperature between about 85 to 90 degrees Fahrenheit; a light cycle of 16 hours lights on and 8 hours lights off; and, an airflow standard for a greenhouse environment. Following nine days plant growth in the hydro grow device130, the clones 114 grown in the solar mulch 115 were observed to have roots about 2×, 3×, 4×, 5× or longer than the clones 104, 124 grown in the traditional rock wool (FIG. 1). It was also observed that the top growth of the clone 114 grown in solar mulch 115 was considerably greener and much larger (i.e., about 2×, 3×, 4×, 5× larger) (see, e.g., FIG. 1) than those 104, 124 grown in rock wool.

This test was preformed multiple times with the same result. For all of these tests we observed that there was over a 99% survival rating with the solar mulch clones compared to 80% survival rating for the plants grown in rock wool.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments.

One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

We claim:

1. A method for improving plant growth, said method comprising:
    (a) providing a kit having a plant with at least one portion of the plant contained by at least one of a bag and pot filled with a growth media, and including an active polymer forming the at least one of the bag and pot;
(b) touching at least one part of the active polymer to the plant;
(c) growing said plant; and
wherein the active polymer comprises one or more minerals suspended, embedded, or otherwise incorporated in a polymer matrix, the active polymer is operable to absorb light, convert the absorbed light into infrared light, and emit the infrared light, and wherein the one or more minerals comprises silicon carbide present in a ratio of at least 3:2;
wherein said plant exhibits improved growth compared to a control plant grown without said active polymer.

2. The method of claim 1, wherein the active polymer absorbs electromagnetic radiation between 400 nm to 14000 nm wavelength.

3. The method of claim 1, wherein the active polymer polarizes electromagnetic radiation between 400 nm to 14000 nm wavelength.

4. The method of claim 1, wherein the active polymer absorbs electromagnetic radiation and emits light between 200 and 1100 nm wavelength.

5. The method of claim 1, wherein the active polymer comprises one or more mineral types selected from the group consisting of calcium carbide (CaC2), titanium dioxide ($TiO_2$), aluminum oxide ($Al_2O_3$), and silicon dioxide ($SiO_2$).

6. The method of claim 1, wherein the active polymer comprises one or more polymer types selected from the group consisting of polyethylene terephthalate (PET), polyester, nylon, rayon, and spandex.

7. The method of claim 1, wherein the mineral suspended, embedded or otherwise incorporated in the polymer matrix comprises about 1% to about 2% of a total weight of the active polymer.

8. The method of claim 1, wherein the active polymer is extruded into a form selected from the group consisting of a fiber, a staple fiber, a film, and a sheet.

9. The method of claim 1, wherein the active polymer is placed in contact with the growth media for said plant.

10. The method of claim 8, wherein the selected form of the active polymer is a fiber, and wherein said fiber is made into a textile using a technique selected from the group consisting of weaving, stitching, sewing, knitting, bonding, fusing, and felting.

11. The method of claim 1, wherein the kit comprises a planting container with the active polymer material comprising the polymer matrix and a mineral powder, and the active polymer material lining the inside of the planting container.

12. The method of claim 1, wherein the kit includes the plant being potted.

13. The method of claim 1, wherein the active polymer matrix comprises a mineral powder incorporated into the polymer matrix.

14. The method of claim 1, wherein the kit is in a form of a bagged or potted growth media with the plant embedded in the active polymer material.

15. The method of claim 14, wherein the plant is a clone.

16. The method of claim 14, wherein the plant is in a seedling form.

17. The method of claim 14, wherein the plant is male.

18. The method of claim 14, wherein the plant is female.

19. A method of growing a plant or plant part thereof comprising:
providing a kit in a form of a plant surrounded by growth media with an active polymer material containing the plant and growth media;
positioning the plant or part thereof touching the active polymer material, wherein the active polymer material is operable to absorb light, convert the absorbed light into infrared light, and emit the infrared, and wherein the one or more minerals comprises silicon carbide present in a ratio of at least 3:2, and
growing the plant, wherein said plant exhibits improved growth compared to a control plant grown without said active polymer.

20. The method of claim 19, wherein the active polymer material emits light in a wavelength between about 350 nm to about 800 nm.

21. A method for improving plant growth, said method comprising:
(a) providing a kit having an active polymer, a growth media, and a plant, wherein the active polymer surrounds the plant and growth media and comprises one or more minerals suspended, embedded or otherwise incorporated in a polymer matrix, and wherein the active polymer is operable to absorb light, convert the absorbed light into infrared light, and emit the infrared light, and wherein the one or more minerals comprises silicon carbide present in a ratio of at least 3:2;
(b) touching at least one part of the active polymer to the plant; and
(c) growing said plant, wherein said plant exhibits improved growth compared to a control plant grown without said active polymer.

* * * * *